(12) United States Patent
Barnes et al.

(10) Patent No.: US 12,053,197 B2
(45) Date of Patent: Aug. 6, 2024

(54) SOFT TISSUE CUTTING DEVICE AND METHODS OF USE

(71) Applicant: Mayo Foundation for Medical Education and Research, Rochester, MN (US)

(72) Inventors: Darryl E. Barnes, Eagan, MN (US); Jay Smith, Byron, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 18/139,175

(22) Filed: Apr. 25, 2023

(65) Prior Publication Data

US 2023/0301678 A1      Sep. 28, 2023

Related U.S. Application Data

(60) Continuation of application No. 17/648,627, filed on Jan. 21, 2022, now Pat. No. 11,666,356, which is a
(Continued)

(51) Int. Cl.
*A61B 17/32*       (2006.01)
*A61M 25/10*      (2013.01)
(Continued)

(52) U.S. Cl.
CPC .............. *A61B 17/320036* (2013.01); *A61B 17/320016* (2013.01); *A61B 2017/22061* (2013.01);
(Continued)

(58) Field of Classification Search
CPC .......... A61B 2017/22048; A61B 2017/22051; A61B 2017/22054; A61B 2017/22055;
(Continued)

(56) References Cited

U.S. PATENT DOCUMENTS 2,123,768  A    7/1938    Corsico-Piccolini et al.
3,435,826  A    4/1969    Fogarty
(Continued)

FOREIGN PATENT DOCUMENTS

DE    4444166 A1    6/1996
EP    3193748 A1    7/2017
(Continued)

OTHER PUBLICATIONS

International Search Report and Written Opinion mailed Mar. 25, 2022 in Application No. PCT/US22/70088.
(Continued)

*Primary Examiner* — Sarah W Aleman
(74) *Attorney, Agent, or Firm* — Seager, Tufte & Wickhem LLP

(57) ABSTRACT

Some embodiments provide a soft tissue device, such as a transverse carpal ligament cutting device having one or more balloons that are deflated when the device is in an inactive position and are inflated when the device is in an active position. Other embodiments provide a soft tissue cutting method, such as a method of cutting a transverse carpal ligament that uses a soft tissue cutting device.

15 Claims, 23 Drawing Sheets

Related U.S. Application Data continuation of application No. 16/413,481, filed on May 15, 2019, now Pat. No. 11,259,829, which is a division of application No. 14/854,775, filed on Sep. 15, 2015, now Pat. No. 10,357,272.

(60) Provisional application No. 62/192,770, filed on Jul. 15, 2015, provisional application No. 62/167,543, filed on May 28, 2015, provisional application No. 62/052,208, filed on Sep. 18, 2014.

(51) Int. Cl.
  A61B 17/22 (2006.01)
  A61B 17/30 (2006.01)
  A61B 90/00 (2016.01)

(52) U.S. Cl.
  CPC .............. *A61B 2017/22065* (2013.01); *A61B 2017/306* (2013.01); *A61B 2017/320048* (2013.01); *A61B 2090/0801* (2016.02); *A61B 2217/005* (2013.01); *A61M 25/10182* (2013.11)

(58) Field of Classification Search
  CPC .... A61B 2017/32113; A61B 17/22032; A61B 17/320016; A61B 17/320036; A61B 17/320074; A61B 17/3211; A61M 2025/018; A61M 25/10181
  See application file for complete search history.

(56) References Cited

U.S. PATENT DOCUMENTS

| | | | |
|---|---|---|---|
| 4,962,770 A | 10/1990 | Agee et al. | |
| 4,963,147 A * | 10/1990 | Agee | A61B 17/320036 606/170 |
| 4,979,951 A | 12/1990 | Simpson | |
| 5,089,000 A | 2/1992 | Agee et al. | |
| 5,125,927 A | 6/1992 | Belanger | |
| 5,197,971 A * | 3/1993 | Bonutti | A61B 17/0218 604/164.11 |
| 5,217,007 A | 6/1993 | Ciaglia | |
| 5,306,284 A | 4/1994 | Agee et al. | |
| 5,325,883 A | 7/1994 | Orr | |
| 5,345,927 A | 9/1994 | Bonutti | |
| 5,425,355 A | 6/1995 | Kulick | |
| 5,569,283 A * | 10/1996 | Green | A61B 17/320036 30/162 |
| 5,620,446 A | 4/1997 | McNamara et al. | |
| 5,649,946 A | 7/1997 | Bramlet | |
| 5,655,545 A | 8/1997 | Johnson et al. | |
| 5,690,663 A | 11/1997 | Stephens | |
| 5,690,664 A | 11/1997 | Sauer et al. | |
| 5,702,417 A | 12/1997 | Hermann | |
| 5,707,382 A | 1/1998 | Sierocuk et al. | |
| 5,709,697 A | 1/1998 | Ratcliff et al. | |
| 5,735,865 A | 4/1998 | Schaumann et al. | |
| 5,755,732 A | 5/1998 | Green et al. | |
| 5,766,198 A | 6/1998 | Li | |
| 5,769,865 A * | 6/1998 | Kermode | A61B 17/320036 604/164.11 |
| 5,769,895 A | 6/1998 | Ripamonti | |
| 5,772,680 A | 6/1998 | Kieturakis et al. | |
| 5,779,053 A | 7/1998 | Partika et al. | |
| 5,782,854 A | 7/1998 | Hermann | |
| 5,800,449 A | 9/1998 | Wales | |
| 5,810,806 A | 9/1998 | Ritchart et al. | |
| 5,813,977 A | 9/1998 | Hinchliffe et al. | |
| 5,827,311 A | 10/1998 | Berelsman et al. | |
| 5,860,997 A | 1/1999 | Bonutti | |
| 5,865,728 A | 2/1999 | Moll et al. | |
| 5,893,861 A | 4/1999 | Yumoto | |
| 5,904,699 A | 5/1999 | Schwemberger et al. | |
| 5,908,433 A | 6/1999 | Eager et al. | |
| 5,954,739 A | 9/1999 | Bonutti | |
| 5,957,944 A | 9/1999 | Khuri et al. | |
| 5,968,061 A | 10/1999 | Mirza | |
| 6,004,337 A | 12/1999 | Kieturakis et al. | |
| 6,007,554 A | 12/1999 | Van Ess | |
| 6,012,586 A | 1/2000 | Misra | |
| 6,015,421 A | 1/2000 | Echeverry et al. | |
| 6,017,356 A | 1/2000 | Frederick et al. | |
| 6,019,774 A | 2/2000 | Weiss et al. | |
| 6,030,402 A | 2/2000 | Thompson et al. | |
| 6,080,175 A | 6/2000 | Hogendijk | |
| 6,083,177 A | 7/2000 | Kobren et al. | |
| 6,106,496 A | 8/2000 | Arnissolle | |
| 6,113,617 A | 9/2000 | van der Merwe | |
| 6,117,153 A | 9/2000 | Lary et al. | |
| 6,168,608 B1 | 1/2001 | Echeverry et al. | |
| 6,171,236 B1 | 1/2001 | Bonutti | |
| 6,179,852 B1 | 1/2001 | Strickland et al. | |
| 6,217,602 B1 | 4/2001 | Redmon | |
| 6,258,113 B1 | 7/2001 | Adams et al. | |
| 6,264,604 B1 | 7/2001 | Kieturakis et al. | |
| 6,346,085 B1 | 2/2002 | Schiffman | |
| 6,358,251 B1 | 3/2002 | Mirza | |
| 6,361,543 B1 | 3/2002 | Chin et al. | |
| 6,402,770 B1 | 6/2002 | Jessen | |
| 6,447,529 B2 | 9/2002 | Fogarty et al. | |
| 6,451,042 B1 | 9/2002 | Bonutti | |
| 6,514,272 B1 | 2/2003 | Kieturakis et al. | |
| 6,565,590 B2 | 5/2003 | Kieturakis et al. | |
| 6,592,602 B1 | 7/2003 | Peartree et al. | |
| 6,632,234 B2 | 10/2003 | Kieturakis et al. | |
| 6,685,717 B1 | 2/2004 | Ilic | |
| 6,746,465 B2 | 6/2004 | Diederich et al. | |
| 6,875,183 B2 | 4/2005 | Cervi | |
| 6,896,141 B2 | 5/2005 | McMichael et al. | |
| 7,001,405 B2 | 2/2006 | Kieturakis et al. | |
| 7,037,317 B2 | 5/2006 | Hermann et al. | |
| 7,214,236 B2 | 5/2007 | Kieturakis et al. | |
| 7,329,253 B2 | 2/2008 | Brounstein et al. | |
| 7,331,462 B2 | 2/2008 | Steppe | |
| 7,434,687 B2 | 10/2008 | Itou et al. | |
| 7,476,235 B2 | 1/2009 | Diederich et al. | |
| 7,481,817 B2 | 1/2009 | Sauer | |
| 7,520,886 B2 | 4/2009 | Surti | |
| 7,540,875 B2 | 6/2009 | Jessen | |
| 7,628,798 B1 | 12/2009 | Welborn | |
| 7,708,751 B2 | 5/2010 | Hughes et al. | |
| 7,744,617 B2 | 6/2010 | Lunsford et al. | |
| 7,780,690 B2 | 8/2010 | Rehnke | |
| 7,918,784 B2 | 4/2011 | Wellborn et al. | |
| 7,967,137 B2 | 6/2011 | Fulbrook et al. | |
| 8,052,710 B2 | 11/2011 | Kambin et al. | |
| 8,105,342 B2 | 1/2012 | Onuki et al. | |
| 8,147,487 B2 | 4/2012 | Burbank et al. | |
| 8,177,064 B2 | 5/2012 | McCormick et al. | |
| 8,246,646 B2 | 8/2012 | Kambin et al. | |
| 8,252,013 B2 | 8/2012 | Leibowitz et al. | |
| D666,725 S | 9/2012 | McCormack et al. | |
| 8,257,379 B2 | 9/2012 | Lee | |
| 8,273,098 B2 | 9/2012 | Strickland | |
| 8,282,665 B2 | 10/2012 | Kieturakis et al. | |
| 8,323,278 B2 | 12/2012 | Brecheen et al. | |
| D673,683 S | 1/2013 | McCormack et al. | |
| D674,489 S | 1/2013 | McCormack et al. | |
| 8,348,966 B2 | 1/2013 | McCormack et al. | |
| 8,419,728 B2 | 4/2013 | Klotz et al. | |
| 8,449,478 B2 | 5/2013 | Lee et al. | |
| 8,500,770 B2 | 8/2013 | Echevery et al. | |
| 8,523,891 B2 | 9/2013 | Welborn | |
| 8,579,930 B2 | 11/2013 | Palmer et al. | |
| 8,603,124 B1 | 12/2013 | Hatch | |
| 8,603,738 B2 | 12/2013 | Condeelis et al. | |
| 8,608,738 B2 | 12/2013 | Brecheen et al. | |
| 8,608,763 B1 | 12/2013 | Jurbala | |
| 8,613,745 B2 | 12/2013 | Bleich | |
| 8,652,157 B2 | 2/2014 | McCormack et al. | |
| 8,672,960 B2 | 3/2014 | Briganti et al. | |
| 8,702,654 B2 | 4/2014 | Agee et al. | |
| 8,721,668 B2 | 5/2014 | McCormack et al. | |

(56) References Cited

U.S. PATENT DOCUMENTS

| | | |
|---|---|---|
| 8,746,452 B2 | 6/2014 | Tomes |
| 8,753,364 B2 | 6/2014 | McCormack et al. |
| 8,876,845 B2 | 11/2014 | Suddaby |
| 8,906,040 B2 | 12/2014 | Filipi et al. |
| 8,911,470 B2 | 12/2014 | Mirza et al. |
| 8,951,273 B1 | 2/2015 | Fard |
| 8,992,424 B2 | 3/2015 | Orbay et al. |
| 9,017,354 B2 | 4/2015 | Fink et al. |
| 9,028,516 B2 | 5/2015 | Palmer et al. |
| 9,050,004 B2 | 6/2015 | Diao et al. |
| 9,113,953 B2 | 8/2015 | Smith |
| 9,131,951 B2 | 9/2015 | Mirza et al. |
| 9,168,057 B2 | 10/2015 | Poulsen |
| 9,186,217 B2 | 11/2015 | Goyal |
| 9,532,847 B2 | 1/2017 | Hendrickson et al. |
| 10,206,703 B2 | 2/2019 | Palmer et al. |
| 10,245,062 B2 | 4/2019 | Seymour |
| 10,335,189 B2 | 7/2019 | Aklog et al. |
| 10,357,272 B2 | 7/2019 | Barnes et al. |
| 10,864,055 B2 | 12/2020 | Barnes et al. |
| 11,141,186 B2 | 10/2021 | Aklog et al. |
| 11,259,829 B2 | 3/2022 | Barnes et al. |
| 11,259,837 B2 | 3/2022 | Aklog et al. |
| 11,666,356 B2 | 6/2023 | Barnes et al. |
| 2002/0120211 A1 | 8/2002 | Wardle et al. |
| 2002/0161387 A1 | 10/2002 | Blanco |
| 2002/0185406 A1 | 12/2002 | Massengale et al. |
| 2004/0143280 A1 | 7/2004 | Suddaby |
| 2004/0195131 A1 | 10/2004 | Spolidoro |
| 2005/0209624 A1 | 9/2005 | Vijay |
| 2005/0222598 A1 | 10/2005 | Ho et al. |
| 2005/0228426 A1 | 10/2005 | Campbell |
| 2006/0149136 A1 | 7/2006 | Seto et al. |
| 2006/0190021 A1 | 8/2006 | Hausman et al. |
| 2007/0083225 A1 | 4/2007 | Kiser et al. |
| 2007/0112366 A1 | 5/2007 | Welborn et al. |
| 2007/0118170 A1 | 5/2007 | Kieturakis et al. |
| 2007/0225740 A1 | 9/2007 | Suddaby |
| 2008/0033466 A1 | 2/2008 | Assell et al. |
| 2008/0058588 A1 | 3/2008 | Emanuel |
| 2008/0058846 A1 | 3/2008 | Vosough |
| 2008/0109021 A1 | 5/2008 | Medoff |
| 2008/0195128 A1 | 8/2008 | Orbay et al. |
| 2008/0234713 A1 | 9/2008 | Bernardini |
| 2008/0288041 A1 | 11/2008 | Holman et al. |
| 2009/0048620 A1 | 2/2009 | Weiss et al. |
| 2009/0048623 A1 | 2/2009 | Lafosse et al. |
| 2009/0125044 A1 | 5/2009 | Lary |
| 2009/0171157 A1 | 7/2009 | Diederich et al. |
| 2009/0312740 A1 | 12/2009 | Kim et al. |
| 2009/0312807 A1 | 12/2009 | Boudreault et al. |
| 2010/0010530 A1 | 1/2010 | Rhee |
| 2010/0100114 A1 | 4/2010 | Berger |
| 2010/0125266 A1 | 5/2010 | Deem et al. |
| 2010/0185222 A1 | 7/2010 | Keller |
| 2010/0211082 A1 | 8/2010 | Sauer |
| 2010/0249719 A1 | 9/2010 | Fojtik |
| 2011/0087258 A1 | 4/2011 | Sluss |
| 2011/0112563 A1 | 5/2011 | To et al. |
| 2011/0118601 A1 | 5/2011 | Barnes et al. |
| 2011/0155599 A1 | 6/2011 | Yakel et al. |
| 2011/0201881 A1 | 8/2011 | Emch |
| 2012/0016398 A1 | 1/2012 | Strickland |
| 2012/0029542 A1 | 2/2012 | Huang |
| 2012/0029543 A1 | 2/2012 | Lee |
| 2012/0191116 A1 | 7/2012 | Flynn et al. |
| 2012/0198703 A1 | 8/2012 | Ranieri et al. |
| 2012/0203220 A1 | 8/2012 | Brannan et al. |
| 2012/0289987 A1 | 11/2012 | Wilson et al. |
| 2012/0303018 A1 | 11/2012 | Ladtkow et al. |
| 2013/0046323 A1 | 2/2013 | Whitaker |
| 2013/0066149 A1 | 3/2013 | Mirza et al. |
| 2013/0144318 A1 | 6/2013 | Dinis Carmo |
| 2013/0165962 A1 | 6/2013 | Porshinsky et al. |
| 2013/0172895 A1 | 7/2013 | Wallace et al. |
| 2013/0197553 A1 | 8/2013 | Ng et al. |
| 2013/0211201 A1 | 8/2013 | Wongsiri |
| 2013/0289596 A1 | 10/2013 | Guo |
| 2013/0345515 A1 | 12/2013 | Fitzmaurice |
| 2014/0012076 A1 | 1/2014 | Mirza et al. |
| 2014/0031621 A1 | 1/2014 | Liu |
| 2014/0039533 A1 | 2/2014 | Palmer et al. |
| 2014/0054356 A1 | 2/2014 | Hartwick et al. |
| 2014/0066709 A1 | 3/2014 | Mirza et al. |
| 2014/0121456 A1 | 5/2014 | McCormack et al. |
| 2014/0180282 A1 | 6/2014 | Brecheen et al. |
| 2014/0276741 A1 | 9/2014 | McKay |
| 2014/0276790 A1 | 9/2014 | Raybin et al. |
| 2014/0343357 A1 | 11/2014 | Mirza et al. |
| 2014/0371526 A1 | 12/2014 | Mirza et al. |
| 2015/0045822 A1 | 2/2015 | Mirza et al. |
| 2015/0073461 A1 | 3/2015 | McCormack et al. |
| 2015/0080878 A1 | 3/2015 | Feng et al. |
| 2015/0080905 A1 | 3/2015 | Begemann et al. |
| 2015/0133982 A1 | 5/2015 | Park |
| 2015/0182248 A1 | 7/2015 | Palmer et al. |
| 2015/0196743 A1 | 7/2015 | Diederich et al. |
| 2015/0201959 A1 | 7/2015 | Guo |
| 2015/0265818 A1 | 9/2015 | Piskun et al. |
| 2015/0282832 A1 | 10/2015 | Mirza et al. |
| 2015/0320436 A1 | 11/2015 | Agee et al. |
| 2016/0038172 A1 | 2/2016 | Cox |
| 2016/0081710 A1 | 3/2016 | Barnes et al. |
| 2016/0157880 A1 | 6/2016 | Aklog et al. |
| 2016/0235431 A1 | 8/2016 | Brown et al. |
| 2017/0042565 A1 | 2/2017 | Ellsworth et al. |
| 2017/0086803 A1 | 3/2017 | Nakanishi et al. |
| 2017/0105792 A1 | 4/2017 | Barnes et al. |
| 2017/0325797 A1 | 11/2017 | Ladtkow et al. |
| 2018/0338774 A1 | 11/2018 | Pajardi et al. |
| 2019/0262024 A1 | 8/2019 | Barnes et al. |
| 2021/0085416 A1 | 3/2021 | Barnes et al. |
| 2021/0085417 A1 | 3/2021 | Barnes et al. |
| 2022/0218383 A1 | 7/2022 | Barnes |
| 2022/0233232 A1 | 7/2022 | Barnes et al. |

FOREIGN PATENT DOCUMENTS

| | | |
|---|---|---|
| EP | 3278749 A1 | 2/2018 |
| EP | 3766440 A1 | 1/2021 |
| EP | 3908215 A1 | 11/2021 |
| EP | 3975889 A1 | 4/2022 |
| WO | 2007016141 A2 | 2/2007 |
| WO | 2013155472 A1 | 10/2013 |
| WO | 2014118752 A2 | 8/2014 |
| WO | 2014176206 A2 | 10/2014 |
| WO | 2014176206 A3 | 1/2015 |
| WO | 201831617 A1 | 12/2018 |
| WO | 2020247476 A1 | 12/2020 |
| WO | 2022150837 A1 | 7/2022 |
| WO | 2022232582 A1 | 11/2022 |

OTHER PUBLICATIONS

International Search Report and Written Opinion issued Sep. 21, 2020, in International Application No. PCT/US20/35094.

Extended European Search Report for Application No. 20738258.1 dated Feb. 23, 2022.

International Search Report and Written Opinion mailed Jun. 15, 2020, in Application No. PCT/US20/12682.

Trigger Tome® Minimally Invasive Trigger Finger Release System, 1 page, www.sonicsurg.com 2023. Accessed Jun. 26, 2023.

Hebbard et al., "Ultrasound-Guided Microinvasive Carpal Tunnel Release using a Novel Retractable Needle-Mounted Blade: A Cadaveric Study," Journal of Ultrasound Medicine, vol. 37, No. 8, pp. 2075-2081, Aug. 2018.

MicroAire Upper Extremity Carpal Tunnel, https://www.microaire.com 2 pages. Accessed Jun. 26, 2023.

MICROi™ Blade—A Micro Invasive Surgical Instrument, 10 pages. www.microi-tool.com.Accessed Jun. 26, 2023.

(56) References Cited

OTHER PUBLICATIONS

Muramatsu et al., "A Comparison of Blinded Versus Ultrasound-Guided Limited-Open Trigger Finger Release using the Yasunaga Knife," Journal of Hand Surgery, Asian Pacific, vol. 27, No. 1 pp. 124-129, Feb. 2022.
S2S Surgical™ Surgeon-2-Surgeon Innovation, The Future of Minimally Invasive Hand Surgery, 3 pages, 2023.
Summit Medical, About Innovia Medical, 1 page, https://summitmedicalusa.com/ 2023. Accessed Jun. 26, 2023.
Invitation To Pay Additional Fees dated Mar. 31, 2023 for International Application No. PCT/US2023/011838.
International Patent Application No. PCT/US2015/049558, International Search Report and Written Opinion dated Feb. 15, 2016, 24 pages.
U.S. Appl. No. 62/086,950, filed Dec. 3, 2014, unpublished so no copy available.
PCT International Search Report date Dec. 3, 2015 for related International Application No. PCT/US2015/049558, 3 pages.
Examination Report Issued in related European Patent Application No. 15767038.1, dated Apr. 29, 2019, 8 pages.
Information about Related Patents and Patent Applications, see section 6 of the accompanying Information Disclosure Statement Letter, which concerns Related Patents and Patent Applications.

\* cited by examiner

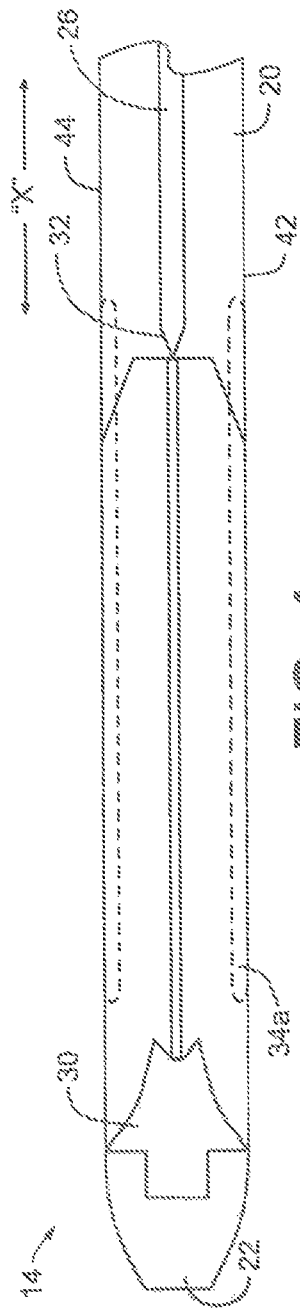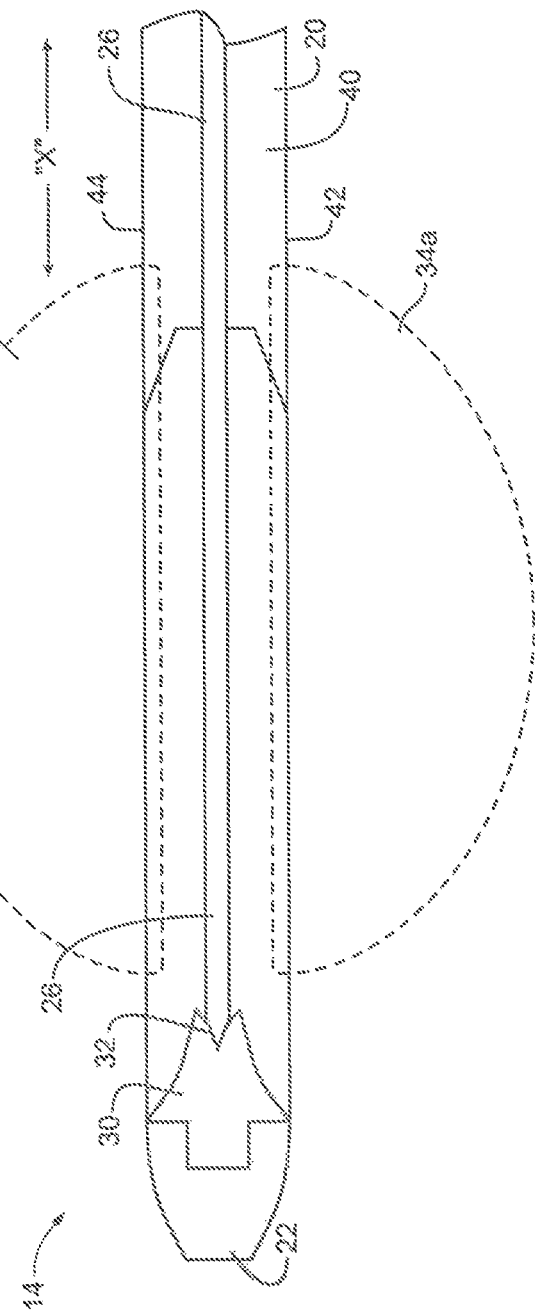

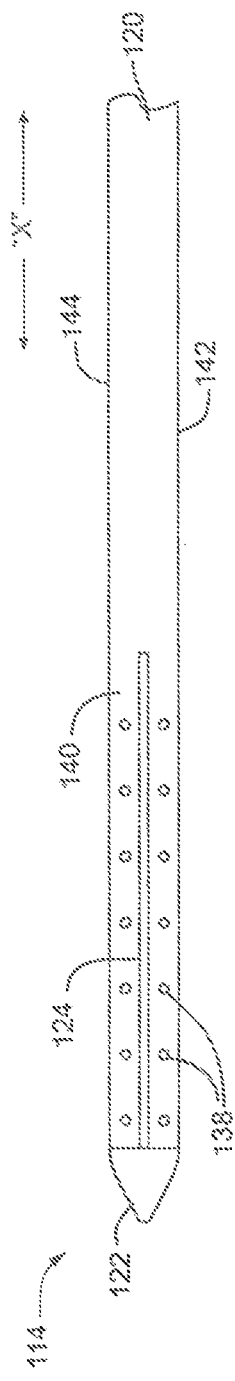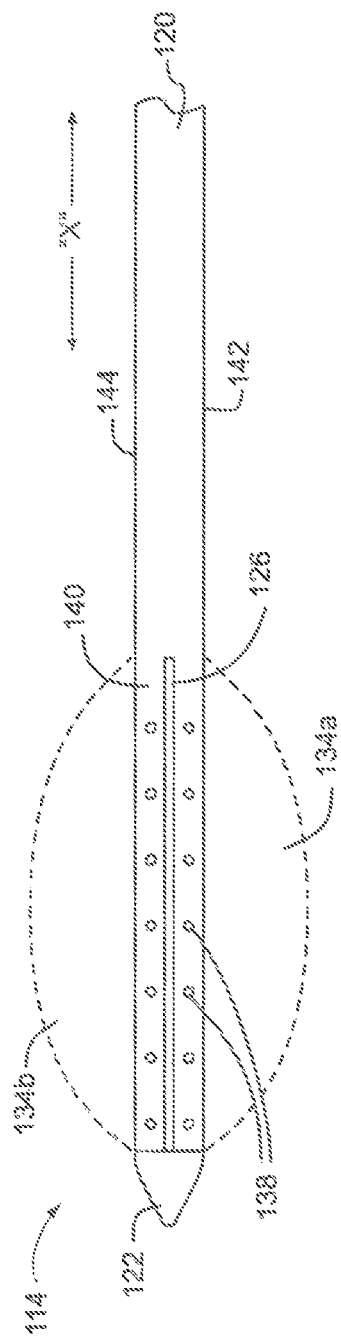

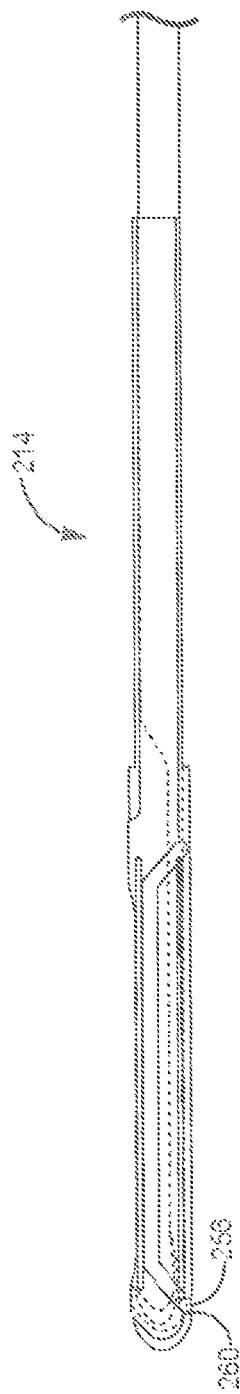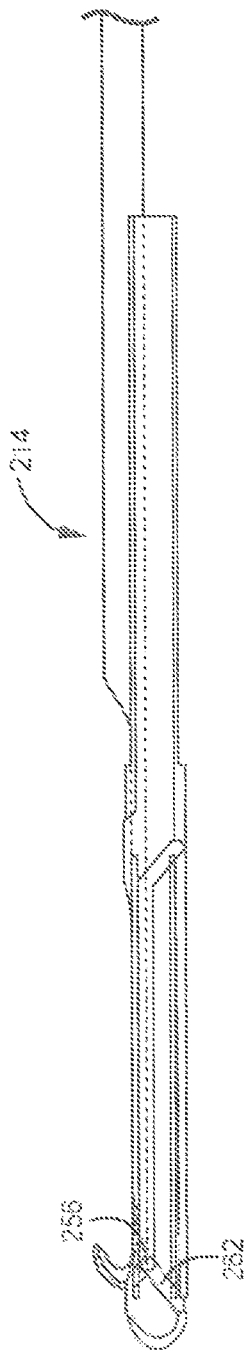

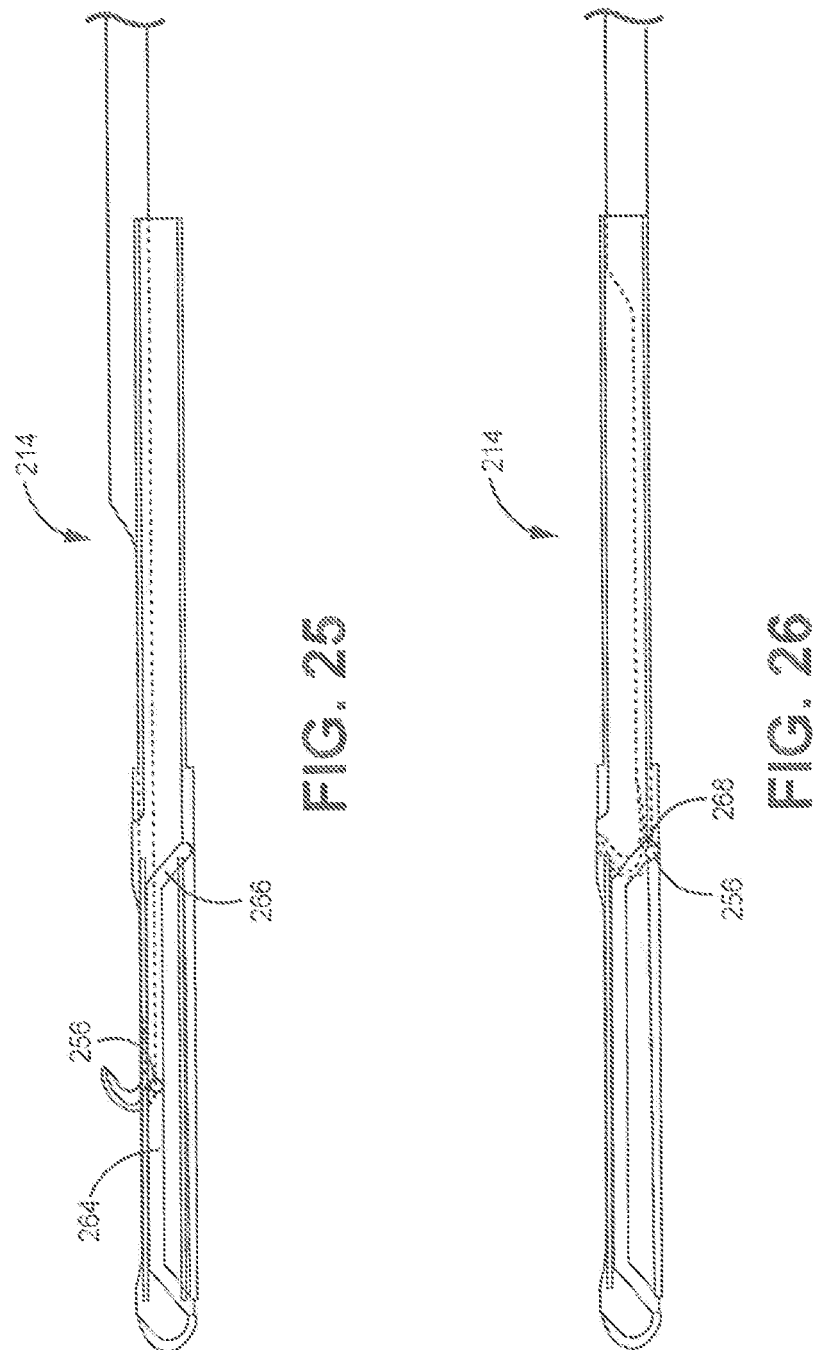

SOFT TISSUE CUTTING DEVICE AND METHODS OF USE

RELATED APPLICATIONS

The present application is continuation application of U.S. application Ser. No. 17/648,627, filed Jan. 21, 2022, which is a continuation application of U.S. application Ser. No. 16/413,481, filed May 15, 2019, which is a divisional application of U.S. application Ser. No. 14/854,775, filed Sep. 15, 2015, and claims priority to U.S. Provisional Application No. 62/052,208, filed Sep. 18, 2014, U.S. Provisional Application No. 62/167,543, filed May 28, 2015 and U.S. Provisional Application No. 62/192,770 filed Jul. 15, 2015, each of which are incorporated herein by reference.

FIELD OF THE INVENTION

The present invention generally relates to a soft tissue cutting device and soft tissue cutting methods. The present invention also relates generally to a transverse carpal ligament cutting device and transverse carpal ligament cutting methods.

BACKGROUND OF THE INVENTION

Carpal tunnel syndrome affects approximately 3.7% of the general population and up to 7% of manual labor workers. Several varying surgical procedures are performed annually to treat patients with carpal tunnel syndrome. One of these surgical procedures is known as a carpal tunnel release procedure ("CTR procedure"). A primary goal of the CTR procedure is to cut a transverse carpal ligament in order to reduce median nerve compression and carpal tunnel pressures in the carpal tunnel region.

CTR procedures can be performed by accessing the carpal tunnel primarily from the outside or accessing the carpal tunnel primarily from the inside. In the former, a palmar incision of various sizes is used to directly visualize and transect the transverse carpal ligament. In the latter, the transverse carpal ligament is visualized from within the carpal tunnel using an endoscope advanced through a small palmar and/or distal wrist incision—endoscopic carpal tunnel release (ECTR).

One concern with CTR procedures is that it is hard to visualize the transverse carpal ligament and at-risk structures nearby (e.g., a median nerve and an ulnar artery). It is also hard to visualize individual anatomical variations in the carpal tunnel region. As a result, some CTR procedures can cause incomplete release of the transverse carpal ligament and others can cause injuries to the nearby at-risk structures.

In recent years, operators have used ultrasound guidance with CTR procedures to better visualize the carpal tunnel region during the procedure. However, even with the improved visualization of ultrasound, there are still concerns even with these procedures. One concern is that a sharp cutting instrument may be passed into the carpal tunnel without the ability to precisely control deployment of a sharp cutting instrument. Thus, the sharp cutting instrument presents a risk to both the patient and the operator. It would be desirable to provide an improved device that includes a sharp cutting instrument that is not exposed until the cutting of the transverse carpal ligament occurs.

Also, several operators use ultrasound guidance to place a sharp cutting instrument in position to cut the transverse carpal ligament but do not utilize ultrasound visualization during the actual cutting. In some cases, this is because the sharp cutting instruments require the use of two hands to perform the cutting. Thus, when operators perform the cutting, they are not able to continue holding the ultrasound probe during cutting. It would be desirable to provide an improved device that allows for an operator to continue using ultrasound guidance during cutting. It would also be desirable to provide a device that allows for an operator to use one hand while cutting, so that the opposite hand can hold an ultrasound probe or otherwise engage in providing ultrasound guidance.

Further, there is typically a very narrow space between the median nerve and the ulnar artery in the carpal tunnel. This narrow space is a "safe zone" in which the transverse carpal tunnel ligament can be cut without risk to the median nerve or ulnar artery. This space is variable from patient to patient and can be less than 3 millimeters in some patients. Consequently, placing a sharp cutting instrument in this region can expose a patient to risks of injury. It would also be desirable to provide a device that can expand the "safe zone" in a patient to reduce risks of injury.

SUMMARY

Some embodiments provide a soft tissue device having (a) a shaft having a top surface, two side surfaces and a bottom surface, wherein the shaft extends along a longitudinal axis, (b) a shaft opening that extends for a distance along the longitudinal axis, (c) a blade that extends through and withdraws from the shaft opening, and (d) one or more balloons coupled to the shaft that expand radially outwardly from the shaft.

Other embodiments provide a transverse carpal ligament cutting device having (a) a shaft having a top surface, two side surfaces and a bottom surface, (b) a shaft opening that extends for a distance along the top surface, (c) a blade having a top cutting edge, and (d) one or more balloons coupled to the shaft that expand radially outwardly from the shaft, wherein the top cutting edge is housed within the shaft and the one or more balloons are deflated when the device is in an inactive position and wherein the top cutting edge extends upwardly through the shaft opening and the one or more balloons are inflated when the device is in an active position.

Other embodiments provide a transverse carpal ligament cutting device having (a) a shaft having a top surface, two side surfaces and a bottom surface, (b) a shaft opening that extends for a distance along the top wall and two side surfaces, (c) a blade having a distal cutting edge, and (d) one or more balloons coupled to the shaft that expand radially outwardly from the shaft, wherein the distal cutting edge is housed within the shaft and the one or more balloons are deflated when the device is in an inactive position and wherein the distal cutting edge extends distally through the shaft opening and the one or more balloons are inflated when the device is in an active position.

Other embodiments provide a transverse carpal ligament cutting device having (a) a shaft having a top surface, two side surfaces and a bottom surface, (b) a shaft opening that extends for a distance along the top wall, (c) a blade having a blade working end, wherein the blade working end includes a cutting edge that faces the proximal end of the device, and (d) a blade guideway within the shaft, wherein the blade working end moves along the blade guideway.

Other embodiments provide a soft tissue cutting device having (a) a shaft having a plurality of surfaces, (b) a shaft opening that extends for a distance along one of the plurality of surfaces, (c) a blade that extends through and withdraws from the shaft opening, (d) an inflation device, a conduit and a balloon, wherein the balloon is coupled to the conduit and the conduit is coupled to the inflation device and wherein the balloon expands radially outwardly from the shaft.

Other embodiments provide a soft tissue cutting method, comprising the steps of: (1) providing a soft-tissue cutting device having (a) a shaft, (b) a shaft opening in the shaft, (c) a blade that extends through and withdraws from the shaft opening, and (d) one or more balloons coupled to the shaft that expand radially outward from the shaft, (2) advancing the soft-tissue cutting device to a body region, (3) expanding the one or more balloons radially outward, and (4) extending the blade through the shaft opening to cut the soft tissue.

Other embodiments provide a method of cutting a transverse carpal ligament, comprising the steps of: (1) providing a cutting device having an inactive position and an active position, wherein in the inactive position the device includes an unexposed blade and one or more deflated balloons and in the active position the device includes an exposed blade and one or more inflated radially-expanding balloons, (2) advancing the device to a carpal tunnel region while the device is in the inactive position, and (3) cutting a transverse carpal ligament while the device is in the active position.

BRIEF DESCRIPTION OF THE DRAWINGS

The following drawings are illustrative of particular embodiments of the invention and therefore do not limit the scope of the invention. The drawings are not necessarily to scale (unless so stated) and are intended for use in conjunction with the explanations in the following detailed description. Embodiments of the invention will hereinafter be described in conjunction with the appended drawings, wherein like numerals denote like elements.

FIG. 4 illustrates top cross-section view of a distal end of a soft tissue cutting device according to a first embodiment, wherein the device is in an inactive position.

FIG. 5 illustrates top cross-section view of a distal end of a soft tissue cutting device according to a first embodiment, wherein the device is in an active position.

FIG. 10 illustrates top cross-section view of a distal end of a soft tissue cutting device according to a second embodiment, wherein the device is in an inactive position.

FIG. 11 illustrates top cross-section view of a distal end of a soft tissue cutting device according to a second embodiment, wherein the device is in an active position.

FIG. 22 illustrates a side cross-section view of a shaft at a distal end of a soft tissue cutting device according to a third embodiment.

FIG. 23 illustrates a side cross-section view of a shaft at a distal end of a soft tissue cutting device according to a third embodiment, wherein the device is in first inactive position.

FIG. 24 illustrates a side cross-section view of a shaft at a distal end of a soft tissue cutting device according to a third embodiment, wherein the device is in an active position.

FIG. 25 illustrates a side cross-section view of a shaft at a distal end of a soft tissue cutting device according to a third embodiment, wherein the device is also in an active position.

FIG. 26 illustrates a side cross-section view of a shaft at a distal end of a soft tissue cutting device according to a third embodiment, wherein the device is in a second inactive position.

DETAILED DESCRIPTION

Figure 1:
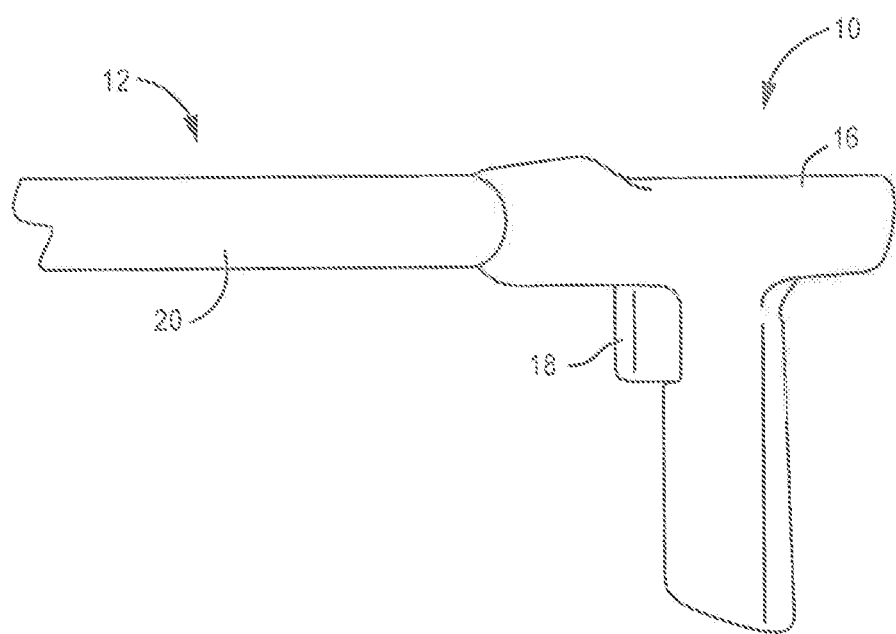
FIG. 1 illustrates a side cross-section view of a proximal end of a soft tissue cutting device according to an embodiment.

Certain embodiments of the invention provide a soft tissue cutting device. The device includes a proximal end and a distal end. The proximal end is configured to enable an operator to control various functions on the distal end. The distal end is configured to perform various functions, including cutting soft tissue in a body. The soft tissue cutting device can be used to cut any desired soft tissue in the body. In certain embodiments, the soft tissue cutting device is a transverse carpal ligament cutting device that cuts a transverse carpal ligament in a carpal tunnel region.

The device includes a proximal end. The proximal end includes one or more controls that control various functions on the distal end. For example, in some embodiments, the controls activate movement of a blade. In other embodiments, the controls activate inflating and deflating of balloons. In yet other embodiments, the controls activate suction through a passage.

In some embodiments, the proximal end includes a single-hand handpiece. The single-hand handpiece has a configuration that allows an operator to operate the device using a single hand only. In some embodiments, the single-hand handpiece is configured as a gun-like handpiece. In some cases, the single-hand handpiece is a gun-like handpiece that includes the one or more controls in a trigger area such that the operator can grip the handpiece while operating the one or more controls with fingers. In other embodiments, the single-hand handpiece is configured as a handle. In some cases, the single-hand handpiece is a handle that includes one or more controls in a thumb area such that the operator can use a thumb to operate one or more controls. In yet other embodiments, the single-hand handle also includes one or more clamp-like controls in an area such that the operator can use a hand to clamp the controls. In some embodiments, the single-hand handpiece is a handle that includes one or more controls on an inferior position of the handle such that the operator can use a finger to operate one or more controls. However, skilled artisans will understand that the single-hand handpiece is merely one embodiment of the present invention and is not required. Alternately, two hands or even two operators can operate the present device.

The handpiece is coupled to a shaft that extends distally towards a distal end. The handpiece can be coupled to the shaft using a variety of different configurations. In some cases, the handpiece and shaft have a permanent junction. For example, the handpiece and shaft can have a set angular junction or a set straight junction. In other cases, the handpiece and shaft have an adjustable junction that can be adjusted to accommodate operator preference. In other cases, the handpiece and shaft have a rotatable junction that can be rotated to accommodate operator preference. For example, the handpiece and shaft can have a junction that is adjustable in length or angulation or rotation. In yet other cases, the handpiece and the shaft can have a removable junction so that the handpiece and the shaft are removable from one another.

The shaft has any desired cross-section shape. In some cases, the shaft has a circular cross-section shape. In other cases, the shaft has a non-circular cross section shape. For example, in some cases, the shaft has a squared cross section shape, rectangular cross section shape or squared with round edges cross section shape.

As the shaft extends from the proximal end towards the distal end, it can maintain the same cross-section shape or it can assume a different cross-section shape. For example, in some cases, as the shaft extends from the proximal end to the distal end, it maintains a circular cross-section. In other cases, as the shaft extends from the proximal end to the distal end, it changes from a circular cross-section to a non-circular cross section. In yet other cases, as the shaft extends from the proximal end to the distal end, it maintains a non-circular cross section. In further cases, as the shaft extends from the proximal end to the distal end, it changes from a non-circular cross-section to a circular cross-section.

The shaft can also be provided as a single piece or as a plurality of different pieces. In some cases, the shaft extends from the proximal end to the distal end as a single piece. In other cases, the shaft extends from the proximal end to the distal end as a plurality of piece. The shaft is also formed of any desired medically acceptable material.

The shaft also has any desired size that is suitable for the medical procedure being performed. As the shaft extends from the proximal end to the distal end, it can maintain the same diameter or it can assume a different diameter. In some cases, as the shaft extends from the proximal end to the distal end, it increases in diameter. In other cases, as the shaft extends from the proximal end to the distal end, it increases in diameter.

The device also includes a distal end. The distal end is the working end that inserts into the body region of a patient. The distal end includes the shaft, a tip, a shaft opening, a blade, and one or more radially expanding balloons. In some cases, the distal end also includes one or more suction openings.

The shaft at the distal end has a size and cross-section shape that is suitable for being inserted into the body region of interest. The shaft extends longitudinally along a longitudinal axis. The shaft also has a top surface, side surfaces and a bottom surface. Each of the top surface, side surfaces, and bottom surface can be made up of a single wall or a plurality of walls. Additionally, each wall can be a straight wall or a curved wall. In some cases, the shaft is circular, such that the top quarter of the circle forms the top surface, the bottom quarter of the circle forms the bottom surface, and the remaining quarters form the side surfaces. In other cases, the shaft is non-circular. The shaft also has a surface that is destined to be positioned adjacent (or even in direct contact with) the soft tissue being cut. In some cases, the top surface is the surface destined to be positioned adjacent the soft tissue.

The distal end also includes a tip. The tip is the distal-most end of the device and is positioned distally to the shaft. In some cases, the tip is an extension of the shaft. In other cases, the tip is a separate piece that is positioned on the distal end of the shaft. The tip can have any size or shape that guides the distal end to the body region. In some embodiments, the tip has a rounded configuration, ovoid configuration, pointed configuration or conical configuration. In some embodiments, the tip is an echogenic tip and includes an ultrasound probe, camera or one or more optical fiber elements to transmit light to or from the distal region of the tip to the proximal portion of the device and is sized and shaped to house an ultrasound probe, camera or one or more optical fiber elements.

The shaft also includes a shaft opening. The shaft opening extends along a longitudinal axis for a distance longitudinally along the shaft. The shaft opening also extends along the shaft surface that is destined to be positioned adjacent to or in direct contact with the soft tissue being cut. In some embodiments, the shaft opening extends longitudinally along the top surface and two side surfaces, so that the shaft opening is open superiorly, medially and laterally. This results in an "open" shaft opening. In other embodiments, the shaft opening extends longitudinally only along the top surface, so that the shaft opening is only open superiorly. This results in a "closed" shaft opening.

The shaft also houses a blade. The blade includes a working end that has a cutting edge that is configured to cut the soft tissue. The cutting edge can have any desired configuration that cuts soft tissue. In some cases, the cutting edge has a sharp straight edge. In other cases, the cutting edge has a sharp curved edge. In yet other cases, the cutting edge has an angulated, toothed or sawed edge. The cutting edge extends through the shaft opening when the device is in an active position and is protected within the shaft when the device is in an inactive position.

The cutting edge can also be positioned on any surface of the blade. In some cases, the blade working end is linear and the cutting edge is provided on a distal edge. In other cases, the blade working end is linear and the cutting edge is provided on a top edge. In other cases, the blade working end is configured as a hook and the cutting edge is provided on an interior surface of the hook. In other cases, the blade has two cutting surfaces allowing the blade to cut when pushed or pulled through soft tissue.

The blade is also movable with respect to the shaft using any number of different mechanisms. In some cases, the blade is movable by inflating and deflating a blade balloon elevator. The blade balloon elevator raises the blade out of the shaft and lowers the blade back into the shaft. In other cases, the blade is movable by moving the blade along a blade guideway. The blade guideway can also have a number of different configurations. For example, in some cases, the blade guideway is a substantially flat guide rail. In other cases, the blade guideway includes one or more ramps or inclines.

In other cases, the blade guideway has an adjustable height, allowing an operator to increase or decrease cutting depths. Different patients have different transverse carpal tunnel thicknesses and an adjustable blade guideway allows an operator to adjust for these different thicknesses. The blade guideway height can be adjusted using any desired adjustment mechanism. In certain cases, the blade guideway height is adjusted by changing the angle of the ramps or inclines. In other cases, the blade guideway height is adjusted using a balloon elevator.

The shaft also includes one or more balloons that expand radially outwardly from the shaft. The balloons serve a number of different purposes. First, the balloons help to anchor the device within the body region to provide stability during cutting of the soft tissue. Also, the balloons help to push nearby at-risk structures away from the device during cutting. This helps to ensure that only the desired soft tissue is cut and that nearby at-risk structures are not cut.

The shaft can have any desired number of radially-expanding balloons. In some cases, the shaft includes a lateral balloon that expands radially outwardly from one of the two side walls. In other cases, the shaft includes a dorsal balloon that expands radially outwardly from the bottom wall. Skilled artisans will understand that the shaft can have any desired number of lateral and/or dorsal balloons.

In some embodiments, the distal tip includes one or more balloons that expand radially outward from the distal tip. Like the shaft, the distal tip can include any desired number of radially-expanding balloons. In some cases, the distal tip includes a dorsal balloon that expands radially outward from a bottom surface of the tip. These balloons serve the same purposes as the balloons that expand from the shaft.

When inflated, the balloons can have any desired configuration. In some cases, the balloons have a spherical configuration. In other cases, the balloons have an oval configuration. In yet other cases, the balloons have a bilobular configuration.

The balloons can also be inflated and deflated using a number of different techniques. Generally, an inflation device supplies inflation material to inflate the balloons and removes inflation material to deflate the balloons. The inflation material can be a gas (e.g., air) or a liquid or fluid (e.g., water or saline). The balloons can also inflate to a desired size selected to accommodate the patient body area of interest. For example, in some cases, the balloons can be provided with a specific size such that when they are fully inflated, they have a specific inflated size. In other cases, the balloons can have a standard size but can be partially inflated or fully inflated to have a variety of different inflated sizes. In some cases, the balloon inflation can be graded to allow the operator to choose a particular balloon diameter. In certain cases, the balloon inflation can be pressure dependent, such that the balloon manually or automatically inflates until a specific pressure is exerted on the balloon surface.

The inflation device supplies inflation material to the balloons using any desired arrangement. In some cases, the shaft includes one or more conduits operably coupled to both the balloons and the inflation device to deliver and remove gas/fluid to and from the balloons. In some cases, a single conduit is used to deliver and remove gas/fluid to and from the balloons. In other cases, a plurality of conduits can be used. In one example, a first conduit can deliver and remove gas/fluid to and from a first balloon while a second conduit can deliver and remove gas/fluid to and from a second balloon. In another example, a first conduit can deliver gas/fluid to all of the balloons while a second conduit can remove gas/fluid from all of the balloons. Skilled artisans will understand that any arrangement of conduits can be used.

In some embodiments, the distal end also includes a plurality of suction openings. In some cases, the suction openings can be provided along the shaft surface that is destined to be positioned adjacent to or in direct contact with the soft tissue being cut. In many cases, the suction openings are provided along a top surface of the shaft. The suction openings can have any desired configuration. In some cases, the suction openings are circular holes. In other cases, the suction openings are slots. In yet other cases, the suction openings are provided as a single elongated slot that extends along a shaft longitudinal axis.

Suction is applied to the suction openings to suck air through the suction openings. This causes soft tissue near the suction openings to move closer to the surface. Suction can be applied to the suction openings using any desired mechanism. In some cases, the shaft includes one or more conduits operably coupled to the suction openings to apply suction to the suction openings. In some cases, a single conduit is used to apply suction to the suction openings. In other cases, a plurality of conduits can be used. For example, a first conduit can apply suction to some of the suction openings and a second conduit can apply suction to other of the suction openings. Skilled artisans will understand that any arrangement of conduits can be used.

In some embodiments, the distal tip includes a portion that expands and contracts so the tip can be inserted into the body with a smaller cross-section and then expanded once in the body to a larger cross-section. In some cases, the portion that expands and contracts is an outer shell provided on the distal tip. For example, the outer shell can be provided along a portion of the shaft (or the entire shaft) to expand radially outward when positioned in the body to create a greater distance between the central/ventral portion of the device when the knife is exposed during activation. Such an outer shell provides even further protection to the body structures near the tissue being cut. The outer shell can expand and contract using any known mechanism. In some cases, the outer shell includes a firm material. In other cases, the outer shell includes a malleable material. Mechanisms that expand/contract an outer shell include but are not limited to a coil, wedge and sleeve mechanism, a sliding wedge bolt mechanism, an expansion-shell bolt mechanism, slot and wedge bolt mechanism, and a balloon expander/contracter mechanism. Skilled artisans will also understand that any number of outer shells can be provided on the distal tip.

Certain exemplary embodiments of a transverse carpal ligament cutting device 10 will now be described with reference to the Figures. FIGS. 1-7 illustrate a transverse carpal ligament cutting device 10 according to an embodiment. The device 10 has a proximal end 12 and a distal end 14. The proximal end 12 can have any configuration to enable an operator to control various functions on the distal end 14. In some cases, the proximal end 12 includes a single-hand handpiece according to any desired configuration. The distal end 14 is configured to perform various functions, including cutting a transverse carpal ligament in a carpal tunnel region.

FIG. 1 illustrates a side view of a proximal end 12 according to an embodiment. As shown in FIG. 1, the proximal end 12 includes a single-hand handpiece 16. The single-hand handpiece 16 has a configuration that allows an operator to operate the device 10 using a single hand only. The handpiece 16 can have any desired handpiece configuration. In FIG. 1, the handpiece is configured as a gun-like handpiece. However, skilled artisans will understand that the handpiece can instead have any other embodiment described herein for a handpiece. For example, the handpiece can instead be configured as a handle 216 as shown in any of FIGS. 14, 28 and 29.

In FIG. 1, the handpiece 16 is configured as a gun-like handpiece that includes the one or more controls 18 in a trigger area such that the operator can grip the handpiece 16 while operating the one or more controls with fingers. For example, in some embodiments, the controls 18 activate movement of a blade. In other embodiments, the controls 18 activate inflating and deflating of balloons. In yet other embodiments, the controls 18 activate suction through a passage.

The handpiece 16 is coupled to a shaft 20 that extends distally towards a distal end. The handpiece 16 can be coupled to the shaft 20 using a variety of different configurations. In some cases, the handpiece 16 and shaft 20 have a permanent junction. For example, the handpiece 16 and shaft 20 can have a set angular junction or a set straight junction. In other cases, the handpiece 16 and shaft 20 have an adjustable junction that can be adjusted to accommodate operator preference. For example, the handpiece 16 and shaft 20 can have a junction that is adjustable in length or angulation. In yet other cases, the handpiece 16 and the shaft 20 can have a removable junction so that the handpiece 16 and the shaft 20 are removable from one another.

The shaft 20 has any desired cross-section shape. As the shaft 20 extends from the proximal end 12 towards the distal end 14, it can maintain the same cross-section shape or it can assume a different cross-section shape. In some cases, as the shaft 20 extends from the proximal end 12 to the distal end 14, it maintains a circular cross-section. In other cases, as the shaft 20 extends from the proximal end 12 to the distal end 14, it changes from a circular cross-section to a non-circular cross section. In yet other cases, as the shaft 20 extends from the proximal end 12 to the distal end 14, it maintains a non-circular cross section. In further cases, as the shaft 20 extends from the proximal end 12 to the distal end 14, it changes from a non-circular cross-section to a circular cross-section.

The shaft 20 can also be provided as a single piece or as a plurality of different pieces. In some cases, the shaft 20 extends from the proximal end 12 to the distal end 14 as a single piece. In other cases, the shaft 20 extends from the proximal end 12 to the distal end 14 as a plurality of pieces. The shaft 20 is also formed of any desired medically acceptable material.

The shaft 20 also has any desired size that is suitable for performing a CTR procedure. As the shaft 20 extends from the proximal end 12 to the distal end 14, it can maintain the same diameter or it can assume a different diameter. In some cases, as the shaft 20 extends from the proximal end 12 to the distal end 14, it increases in diameter. In other cases, as the shaft 20 extends from the proximal end 12 to the distal end 14, it increases in diameter.

The device 10 includes a distal end 14 that is the working end that inserts into the carpal tunnel region. FIGS. 2-7 illustrate views of a distal end 14 according to one embodiment. The distal end 14 includes a shaft 20, tip 22, a shaft opening 24, a blade 26, a blade guideway 28, a blade stop 30, a first lateral balloon 34a and a second lateral balloon 36b. Each of these components work together to safely cut a transverse carpal ligament in a carpal tunnel region.

The distal end 14 includes a shaft 20 that has a size and cross-section shape that is suitable for being inserted into the carpal tunnel region. The shaft 20 extends longitudinally along a longitudinal axis "x." The shaft 20 has a top surface 40, side surfaces 42, 44, and a bottom surface 46. In this first embodiment, the shaft 20 has a non-circular cross-section such that top surface 40 includes a single top wall, the side surfaces 42, 44 include two side walls, and the bottom surface 44 includes three side walls. Of course, skilled artisans will understand that the shaft 20 can include any other desired cross-section and that each shaft surface can include any desired number of side walls.

The distal end 14 includes a tip 22. The tip 22 is the distal-most end of the device 10 and is positioned distally to the shaft 20. In some cases, the tip 22 is an extension of the shaft 20. In other cases, the tip 22 is a separate piece that is positioned on the distal end of the shaft. The tip 22 can have any size or shape that guides the distal end 14 through the carpal tunnel area. In this first embodiment, the tip 22 has a pointed configuration. Of course, the tip 22 can have any other desired configuration. In some embodiments, the tip 22 is an echogenic tip to improve visualization. In some cases, the echogenic tip includes an ultrasound probe and is sized and shaped to house an ultrasound probe.

Figure 2:
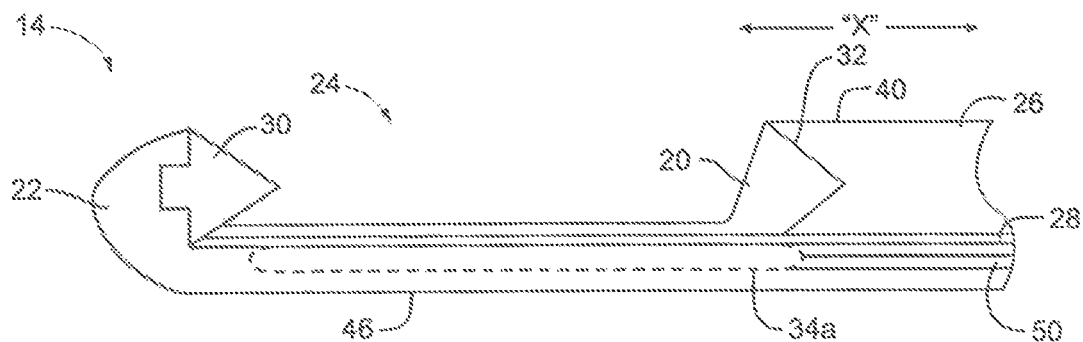
FIG. 2 illustrates a side cross-section view of a distal end of a soft tissue cutting device according to a first embodiment, wherein the device is in an inactive position.

The shaft 20 also includes a shaft opening 24. The shaft opening 24 also extends for a distance longitudinally along the surface that is destined to be positioned adjacent to or in direct contact with the transverse carpal tunnel ligament. In this first embodiment, as best shown in FIG. 2, the shaft opening 24 extends along the top surface 40 and two side surfaces 42, 44 so that the shaft opening 24 is open superiorly, medially and laterally. This results in an "open" shaft opening 24.

The shaft 20 also houses a blade 26. The blade 26 includes a cutting edge 32 that is configured to cut a transverse carpal ligament. In this first embodiment, the cutting edge 32 is a distal most edge of the blade 26. The cutting edge 32 can have any desired configuration that cuts a transverse carpal ligament. Here, the cutting edge 32 has a sharp angulated edge. However, this is not required and the cutting edge 32 can have any other desired configuration.

The shaft 20 also includes a blade guideway 28 that guides movement of the blade 26. The blade guideway 28 can be configured as a guide rail or as a tunnel. In the illustrated embodiment, the blade guideway 28 is configured as a guide rail that extends in a direction parallel to the longitudinal axis x. Also, the guide rail is a substantially flat guide rail. Additionally, the shaft 20 includes a blade stop 30 that stops movement of the blade 26. In some cases, the blade stop 30 is sized and shaped to receive the cutting edge 32.

The blade 26 moves longitudinally along the "x" axis along the guide rail 28 in a forward distal direction and backward proximal direction. As the blade 26 moves forward distally, the cutting edge 32 moves towards the blade stop 30. Likewise, as the blade 26 moves backward proximally, the cutting edge 32 moves away from the blade stop 30. The blade 26 can perform cutting as an operator moves the blade proximally or distally or both.

The shaft 20 also includes one or more balloons that expand or inflate radially outwardly from the shaft 20. This first embodiment illustrates two lateral balloons 34a, 34b. The balloons 34a, 34b inflate and expand outward laterally from the shaft 20. Likewise, the balloons 34a, 34b deflate and shrink inwardly toward the shaft 20. When inflated, the balloons 34a, 34b have a spherical, oval, bilobular or other configuration. When deflated, the balloons 34a, 34b are generally flush with the shaft 20.

Skilled artisans will understand that any number of radially expanding balloons can be used and be placed anywhere about the shaft 20 to secure the distal end 14 in position within the carpal tunnel region and to expand the "safe zone." As the radially expanding balloons inflate, they move the flexor tendons, median nerve, and ulnar neurovascular bundle away from the device 12, effectively increasing the "safe zone." This helps to ensure that only the transverse carpal ligament is cut and that nearby at-risk structures are not cut.

In some embodiments, the distal tip 22 includes one or more balloons that expand radially outward from the distal tip 22. The first embodiment does not use such a distal tip balloon. However, skilled artisans will understand that such a distal tip balloon can be used to increase the distal "safe zone" between the tip and the superficial palmar arch and/or further pushes the tip superiorly (i.e. palmarly) to engage the distal end of the transverse carpal ligament.

The balloons 34a, 34b can also be inflated and deflated using a number of different techniques. In some cases, an inflation device supplies an inflation material to the balloons. The inflation material can be a gas (e.g., air) or a fluid or liquid (e.g., water or saline).

The inflation device supplies inflation material to the balloons 34a, 34b using any desired arrangement. In some cases, the shaft includes one or more conduits operably coupled to both the balloons and the inflation device to deliver and remove gas/fluid to and from the balloons. In the first embodiment, the shaft 20 includes a conduit 50 that delivers and removes gas or fluid from the balloons 34a, 34b. Of course, skilled artisans will understand that other conduit arrangements and other mechanisms of inflating and deflating the balloons 34a, 34b can be used.

The balloons 34a, 34b can be made expandable using any number of desired configurations. In some cases, the entire balloon is expandable and thus inflates and deflates. In other cases, only part of the balloon is expandable. For example, the balloon can have a fixed portion and an expandable portion. The fixed portion can be the portion that directly attaches to a conduit whereas the expandable portion does not directly attach to a conduit and instead expands freely of the conduit.

The balloons 34a, 34b also inflate to a desired size selected to accommodate the size of a patient's wrist (and thus the patient's carpal tunnel region). For example, in some cases, the balloons can be provided with a specific size such that when they are fully inflated, they have a specific inflated size. In one embodiment, each of the balloons 34a, 34b inflate to a similar or same diameter (e.g., a diameter of about 1.5 mm). In patients with larger wrists, larger balloons can be used. In patients with smaller wrists, smaller balloons can be used. In another embodiment one of the balloons 34a, 34b inflates to one size and the other inflates to a different size. In other cases, the balloons 34a, 34b can have a standard size but can be partially inflated or fully inflated to have a variety of different inflated sizes. In some cases, the balloon inflation can be graded to allow the operator to choose a particular balloon diameter. In certain cases, the balloon inflation can be pressure dependent, such that the balloon manually or automatically inflates until a specific pressure is exerted on the balloon surface.

Figure 6:
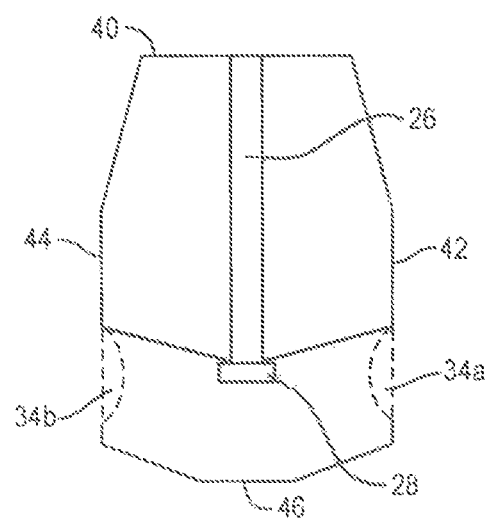
FIG. 6 illustrates a front cross-section view of a soft tissue cutting device according to a first embodiment, wherein the device is in an inactive position.

FIGS. 2, 4 and 6 show the distal end 14 in an inactive position. In the inactive position, the blade 26 is positioned such that its cutting edge 32 is protected within the shaft 20 and is positioned proximally from the "open" shaft opening 24. The balloons 34a, 36b are also deflated. In this inactive position, the blade 26 is not exposed and does not pose any risk to the operator or the patient. Thus, the operator inserts and removes the distal end 14 into and from the carpal tunnel region when it is in the inactive position.

Figure 3:
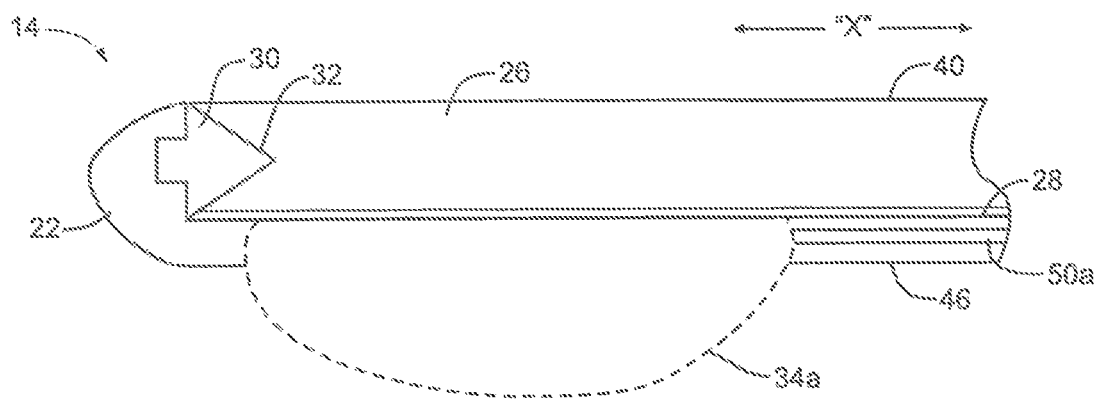
FIG. 3 illustrates a side cross-section view of a distal end of a soft tissue cutting device according to a first embodiment, wherein the device is in an active position.
Figure 7:
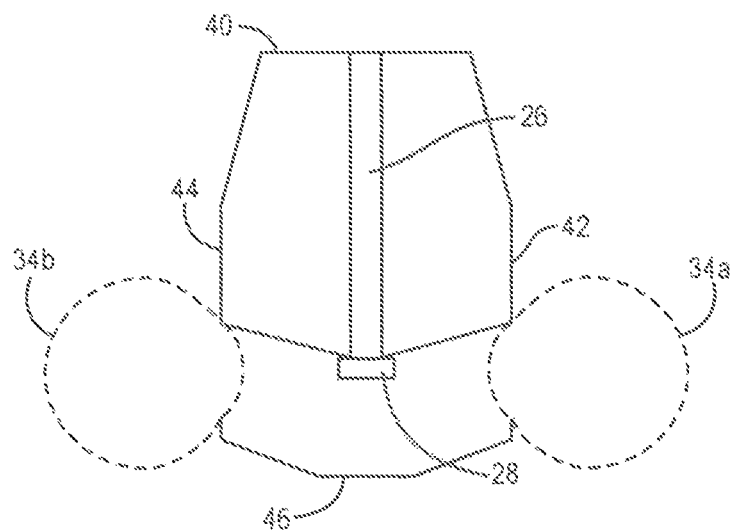
FIG. 7 illustrates a front cross-section view of a soft tissue cutting device according to a first embodiment, wherein the device is in an active position.

FIGS. 3, 5 and 7 show the distal end 14 in an active position. In the active position, the blade 26 is positioned such that its cutting edge 32 is within the shaft opening 24. In the active position, the blade 26 is exposed and is able to cut the transverse carpal ligament. The balloons 34a, 34b are also inflated to anchor the distal end 14 in position within the body and to expand the "safe zone" while the blade 26 performs cutting.

During use, an operator inserts the distal end in an inactive position into the carpal tunnel region so that the transverse carpal ligament is positioned within the shaft opening 24 and the tip 22 is hooked around a distal end of the transverse carpal ligament. The operator then activates a control to cause the balloons 34a, 34b to inflate. The inflated balloons 34a, 34b stabilize the distal end 14 in position within the carpal tunnel region and expand the "safe zone."

The operator next activates a control to cause the blade 26 cut the transverse carpal ligament. In one embodiment, the operator moves the blade 26 backward distally along the guideway 28 so that its cutting edge 32 moves backward away from the blade stop 30 and into the covered shaft 20. As the blade 26 moves proximally, the cutting edge 32 cuts the transverse carpal ligament that is positioned within the shaft opening 24. Once the cutting edge 32 moves into the covered shaft 20, the ligament is completely cut. The operator can repeat this process as necessary.

In another embodiment, the operator activates a control to cause the blade 26 to move forward distally along the guideway 28 so that its cutting edge 32 moves toward the blade stop 30. As the blade 26 moves distally, the cutting edge 32 cuts the transverse carpal ligament that is positioned within the shaft opening 24. The blade stop 28 stops the cutting edge 32 from moving any further distally. Once the cutting edge 32 engages the blade stop 30, the ligament is completely cut. The operator can then repeat this process as necessary.

Once the transverse carpal ligament has been cut and the blade 26 is moved back into the covered shaft 20, the operator then activates a control to cause the balloons 34a, 34b to deflate. The distal end 14 resumes an inactive position and the operator can then safely remove the distal end 14 from the body.

FIGS. 8-13 illustrate views of a transverse carpal ligament cutting device 100 according to another embodiment. The device 100 has a proximal end (not shown) and a distal end 114 that inserts into the carpal tunnel region. The proximal end 12 includes a single-hand handpiece according to any desired configuration. The single-hand handpiece 16 has a configuration that allows an operator to operate the device 10 using a single hand only. Skilled artisans will understand that the handpiece can have any of the embodiments described herein for a handpiece, including the handpiece shown in each of FIGS. 1, 14, 28 and 29.

The proximal end is coupled to a shaft 120 that extends distally towards a distal end 114. The shaft 120 can have any embodiment already described for shaft 20. The proximal end can have any desired configuration to allow an operator to control various functions on the distal end 114. The distal end 114 includes a shaft 120, a tip 122, a shaft opening 124, a blade 126, an optional blade base plate 128, a blade elevator balloon 130, a first lateral balloon 134a, a second lateral balloon 134b, a dorsal balloon 136 and a plurality of suction holes 138. Each of these components work together to safely cut a transverse carpal ligament in a carpal tunnel region.

The distal end 114 includes a shaft 120 that has a size and cross-section shape that is suitable for being inserted into the carpal tunnel region. The shaft 210 extends longitudinally along a longitudinal axis "x." The shaft 120 has a top surface 140, side surfaces 142, 144, and a bottom surface 146. In this second embodiment, the shaft 120 has a non-circular cross-section such that top surface 140 includes a single top wall and the side surfaces 142, 144 and the bottom surface 44 includes a curved side wall. Of course, skilled artisans will understand that the shaft 120 can include any other desired cross-section and that each shaft surface can include any desired number of side walls.

The distal end 114 includes a tip 122. The tip 122 is the distal-most end of the device 10 and is positioned distally to the shaft 120. In some cases, the tip 122 is an extension of the shaft 120. In other cases, the tip 122 is a separate piece that is positioned on the distal end 114 of the shaft 120. The tip 122 can have any size or shape that guides the distal end 114 through the carpal tunnel area. In this second embodiment, the tip 122 has a conical configuration. Again, skilled artisans will understand that the tip 122 can have any other desired configuration. In some embodiments, the tip 122 is an echogenic tip that includes an ultrasound probe and is sized and shaped to house an ultrasound probe.

The shaft 120 also includes a shaft opening 124. The shaft opening 124 also extends for a distance longitudinally along the "x" axis. The shaft opening 124 extends along a surface that is destined to be positioned in direct contact with the transverse carpal ligament. In this second embodiment, the top surface 140 is the surface that is destined to be positioned in direct contact with the transverse carpal ligament. As such, the shaft opening 124 extends along the top surface 140 only so that the shaft opening 124 is only open superiorly. This results in a "closed" shaft opening 124.

The shaft 120 also houses a blade 126. The blade 126 includes a cutting edge 132 that is configured to cut a carpal tunnel ligament. In this second embodiment, the cutting edge 132 is a top edge of the blade 126. The cutting edge 132 can have any desired configuration that cuts soft tissue. Here, the cutting edge 132 has a sharp straight edge. The cutting edge 132 can also have any desired length.

The shaft 120 also includes an optional blade base plate 128 that supports the blade 126. The blade base plate 128 attaches to the blade 126 along a bottom edge of the blade. Also, a blade elevator balloon 130 is positioned beneath the blade base plate 128. In some embodiments, the blade 126 is connected directly to the blade elevator balloon 130 (and there is no blade base plate 128). The blade elevator balloon 130 can have any desired configuration, such as a spherical or bilobular configuration.

When the blade elevator balloon 130 inflates, it expands upward, thus moving the blade base plate 128 (if included) and the blade 126 upward. The top cutting edge 132 moves upward through the opening 124 and cuts the overlying transverse carpal ligament. When the blade elevator balloon 130 deflates, it shrinks downward, thus moving the blade base plate 128 (if included) and the blade 126 downward until it is again protected within the shaft 120. The blade elevator balloon 130 can have any desired configuration and size so that it can move the base plate 128 and/or the blade elevator balloon 130 upward and downward.

The shaft 120 also includes a conduit 152 that delivers and removes gas or fluid to and from the blade elevator balloon 130. Of course, skilled artisans will understand that other conduit arrangements and other mechanisms of inflating and deflating the blade elevator balloon 130 can be used.

The blade 126 can be elevated to any desired degree. The degree of elevation also determines the degree of cutting of the overlying transverse carpal ligament. An operator can vary and individualize the degree of cutting of the transverse carpal ligament by varying the degrees of the balloon elevator expansion 130 and thus the base plate 128 elevation.

The distal end 114 also includes a first lateral balloon 134a and a second lateral balloon 134b. The distal end 114 also includes a dorsal balloon 136. The balloons 134a, 134b, 136 inflate and expand outward laterally from the device 112. Likewise, the balloons 134a, 134b, 136 deflate and shrink inwardly toward the device 112. When inflated, the balloons 134a, 134b, 136 have a spherical, oval, bilobular or other configuration. When deflated, the balloons 134a, 134b, 136 are generally flush with the distal end 114.

This embodiment illustrates two lateral balloons and one dorsal balloon. However, skilled artisans will understand that any number of balloons can be used and the balloons can be placed anywhere about the shaft to secure the distal end 114 in position within the carpal tunnel region and to expand the "safe zone."

The balloons 134a, 134b, 136 also inflate to a desired size selected to accommodate the size of a patient's wrist (and thus the patient's carpal tunnel region). For example, in some cases, the balloons 134a, 134b, 136 can be provided with a specific size such that when they are fully inflated, they have a specific inflated size. In one embodiment, each of the balloons 134a, 134b, 136 inflate to a similar or same diameter (e.g., a diameter of about 1.5 mm). In patients with larger wrists, larger balloons can be used. In patients with smaller wrists, smaller balloons can be used. In another embodiment one of the balloons 134a, 134b, 136 inflates to one size and another inflates to a different size. In other cases, the balloons 134a, 134b, 136 can have a standard size but can be partially inflated or fully inflated to have a variety of different inflated sizes. In some cases, the balloon inflation can be graded to allow the operator to choose a particular balloon diameter. In certain cases, the balloon inflation can be pressure dependent, such that the balloon manually or automatically inflates until a specific pressure is exerted on the balloon surface.

The shaft 120 also includes a conduit 150 that delivers and removes gas or fluid from the balloons 134a, 134b, 136. An inflation device (not shown) supplies inflation material such as gas, fluid, water or air to the conduit 150. The inflation device also retracts inflation material from the balloons 134a, 134b, 136 back through the conduit 150 and back into the inflation device. Of course, skilled artisans will understand that other conduit arrangements and other mechanisms of inflating and deflating the balloons 134a, 134b, 136 can be used. For example, in some cases, a separate conduit can connect each balloon to an inflation device. Here then, each the balloons 134a, 134b, 136 would be connected to an inflation device via its own conduit.

The shaft 120 further includes a plurality of suction openings 138. In some cases, the suction openings 138 can be provided along a shaft surface that is destined to be positioned in direct contact with the transverse carpal ligament. In the second embodiment, the top surface 144 is the surface that is destined to be positioned in direct contact with the transverse carpal ligament. As such, the suction openings 138 can be provided along the top surface 144.

The suction openings 138 can have any desired configuration. In the second embodiment, the suction openings 138 are circular holes. Of course, the suction openings 138 can have any other desired shapes such as a plurality of slots or a single slot.

Suction is applied to the suction openings 138 to suck air through the suction openings 138. This causes the transverse carpal ligament to move closer to the top surface 144. Suction can be applied to the suction openings 138 using any desired mechanism. In some cases, the shaft 120 includes a vacuum conduit 154 that sucks air through the suction openings 138. Skilled artisans will understand that one or more conduits can be operably coupled to the suction openings to apply suction to the suction openings 138. In some cases, a single conduit is used to apply suction to the suction openings 138. In other cases, a plurality of conduits can be used. For example, a first conduit can apply suction to some of the suction openings 138 and a second conduit can apply suction to other of the suction openings 138. Skilled artisans will understand that any arrangement of conduits can be used.

Figure 8:
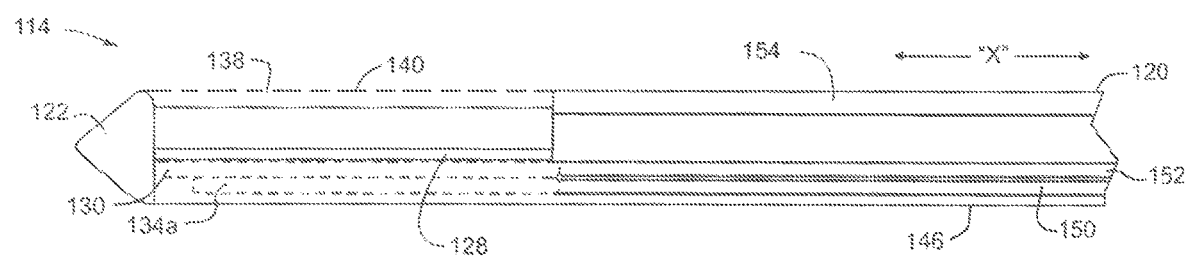
FIG. 8 illustrates a side cross-section view of a distal end of a soft tissue cutting device according to a second embodiment, wherein the device is in an inactive position.
Figure 12:
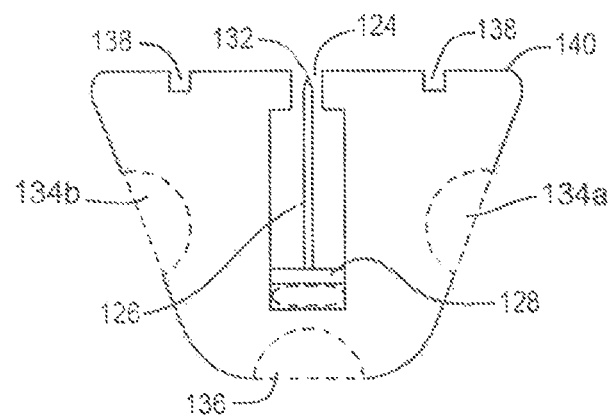
FIG. 12 illustrates a front cross-section view of a soft tissue cutting device according to a second embodiment, wherein the device is in an inactive position.

FIGS. 8, 10 and 12 show the distal end 114 in an inactive position. In the inactive position, the blade 126 is positioned such that its cutting edge 132 is protected within the shaft 120. The balloons 130, 134a, 134b, 136 are also deflated. In this inactive position, the blade 126 is not exposed and does not pose any risk to the operator or the patient. Thus, the operator inserts and removes the distal end 114 into and from the carpal tunnel region when it is in the inactive position.

Figure 9:
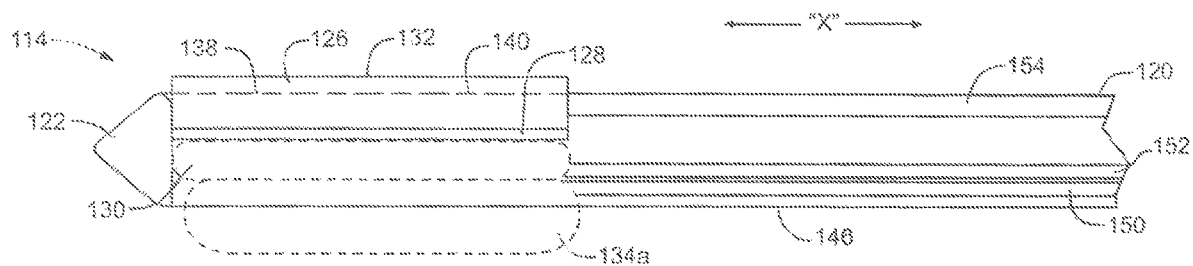
FIG. 9 illustrates a side cross-section view of a distal end of a soft tissue cutting device according to a second embodiment, wherein the device is in an active position.
Figure 13:
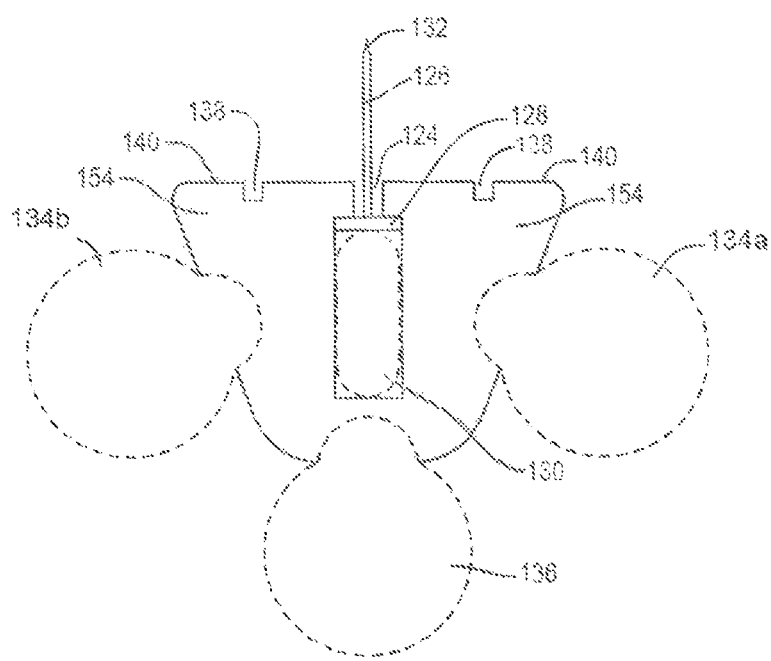
FIG. 13 illustrates a front cross-section view of a soft tissue cutting device according to a second embodiment, wherein the device is in an active position.

FIGS. 9, 11 and 13 show the distal end 114 in an active position. In the active position, blade elevator balloon 130 is inflated and the blade 126 is positioned such that its top cutting edge 132 extends through the superior shaft opening 124 and is exposed. In the active position, the blade 126 is exposed and is able to cut the transverse carpal ligament. The balloons 134a, 134b, 136 are also inflated to anchor the distal end 114 in position within the body and to expand the patient's safe zone while the blade 126 performs cutting.

During use, an operator inserts the distal end 114 into a carpal tunnel region such that the transverse carpal ligament is positioned adjacent the working side 124 of the distal end 114. The operator then activates a control to cause the balloons 134a, 134b, 136 to inflate and to expand the safe zone within the carpal tunnel region. The operator next activates a control to suck air through the suction openings 138. Again, this in turn pulls the transverse carpal ligament towards the top surface 140 to optimize contact between the top surface 140 and the transverse carpal ligament.

The operator next activates a control to cause the balloon elevator to expand so that the cutting edge 132 moves upward through the opening 124 and cuts into the transverse carpal ligament. The depth of the cut can be varied by modulating the extent of the blade elevator balloon 130 inflation. In general, 2-3 mm of upward displacement is sufficient to cut the transverse carpal ligament. The ligament may be completely cut by the upward motion, or may be partially cut/fenestrated by reducing the amount of blade elevation and/or using a blade having a serrated or saw tooth cutting edge 132.

In some cases, once the cutting edge 132 is engaged with the transverse carpal ligament, the operator can manually move the entire device 12 forward distally and backward proximally to impart a sawing motion, as necessary or desired. However, the amplitude of anticipated operator motion should be small given the stabilizing properties of the device.

Once the transverse carpal ligament is cut, the operator activates controls to stop the suction through the suction holes and to deflate all the balloons 134a, 134b, 136. This causes the blade 126 to move back downward into the shaft 120. The operator then safely removes the distal end 114 from the body.

Figure 14:
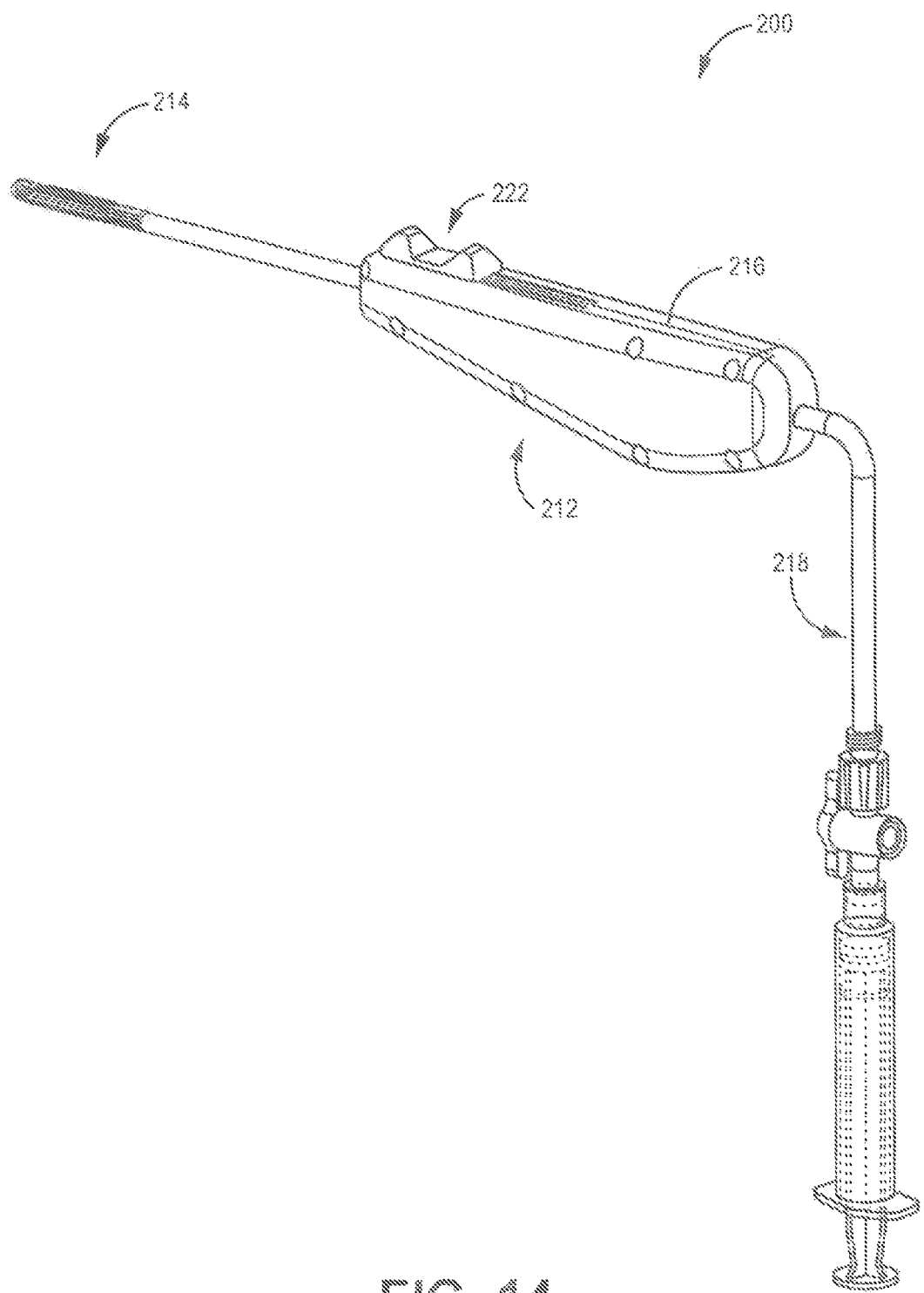
FIG. 14 illustrates a perspective view of a soft tissue cutting device according to a third embodiment.

FIGS. 14-27 illustrate views of a transverse carpal ligament cutting device 200 according to another embodiment. Referring to FIG. 14, the device 200 has a proximal end 212 and a distal end 214. The proximal end 212 includes a handle 216. The distal end 214 includes a shaft 220 that inserts into the carpal tunnel region. The handle 216 includes a blade activation assembly 222. The device 200 also includes an inflation assembly 218 coupled to the handle 216. The inflation assembly 218 and blade activation assembly 222 each control various functions of the shaft 220 at the distal end 214.

Figure 15:
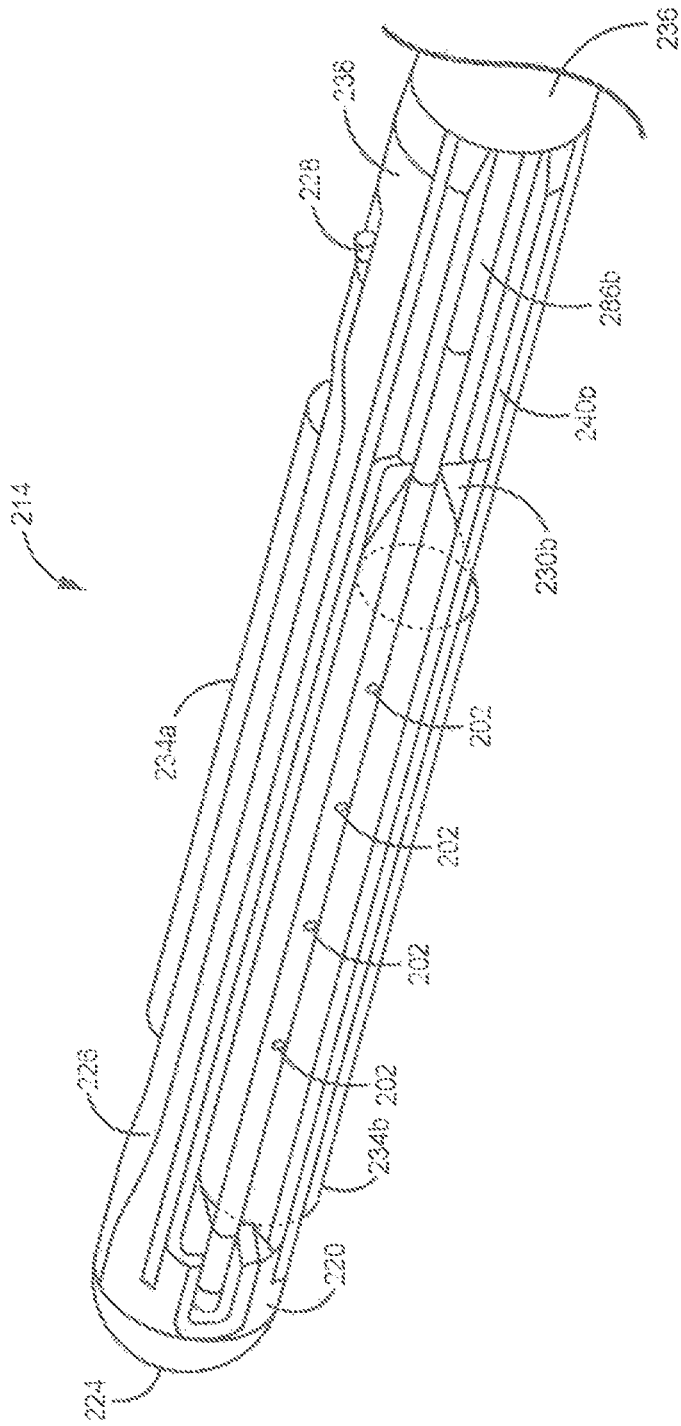
FIG. 15 illustrates a perspective view of a distal end of a soft tissue cutting device according to a third embodiment.
Figure 16:
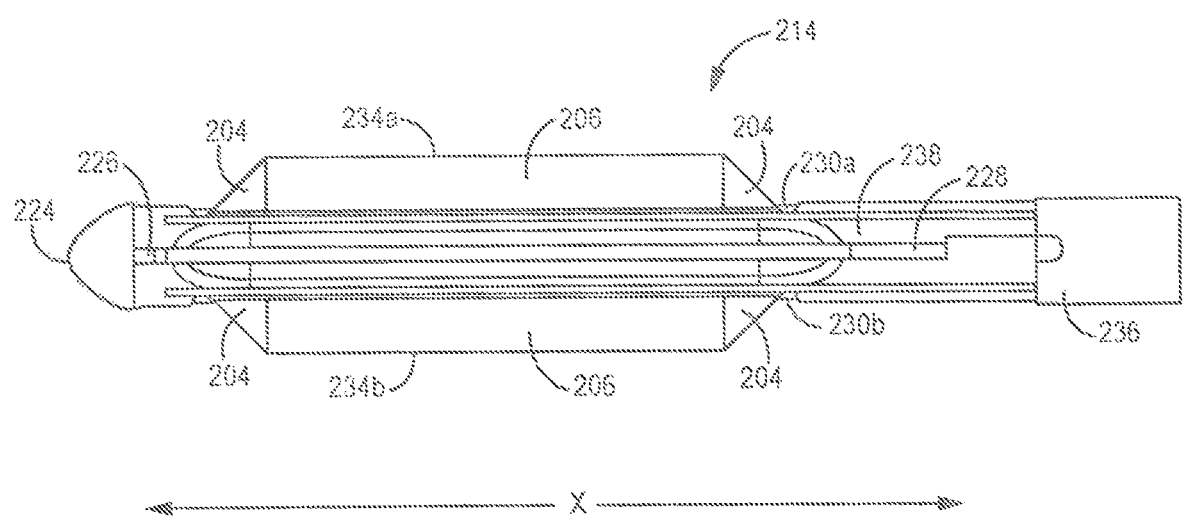
FIG. 16 illustrates a top view of a distal end of a soft tissue cutting device according to a third embodiment.

Referring to FIGS. 15-16, the distal end 214 includes a shaft 220, a tip 224, a shaft opening 226, a blade 228, a first balloon 234a and a second balloon 234b. The shaft 220 can also include a shaft cover 236. The shaft 220 also has a size and cross-section shape that is suitable for being inserted into the carpal tunnel region. The shaft 220 extends longitudinally along a longitudinal axis "x." The shaft 220 has a top surface 238, side surfaces 240a, 240b, and a bottom surface 242. The shaft 220 can also have any embodiment described for shaft 20 or shaft 120.

The distal end 214 includes a tip 224. The tip 224 is the distal-most end of the device 200 and is positioned distally to the shaft 220. In some cases, the tip 224 is an extension of the shaft 220. In other cases, the tip 224 is a separate piece that is positioned on the distal end of the shaft 220. The tip 224 can have any size or shape that guides the distal end 214 through the carpal tunnel area. In this embodiment, the tip 224 has a rounded configuration. Of course, the tip 224 can have any other desired configuration. In some embodiments, the tip 224 is an echogenic tip that includes an ultrasound probe and is sized and shaped to house an ultrasound probe.

The shaft 220 also includes a shaft opening 226. The shaft opening 226 also extends for a distance longitudinally along the surface that is destined to be positioned adjacent to or in direct contact with the transverse carpal tunnel ligament. In this embodiment, as shown in FIGS. 15-16, the shaft opening 226 extends along the top surface 238 so that the shaft opening 226 is open superiorly.

Figure 17:
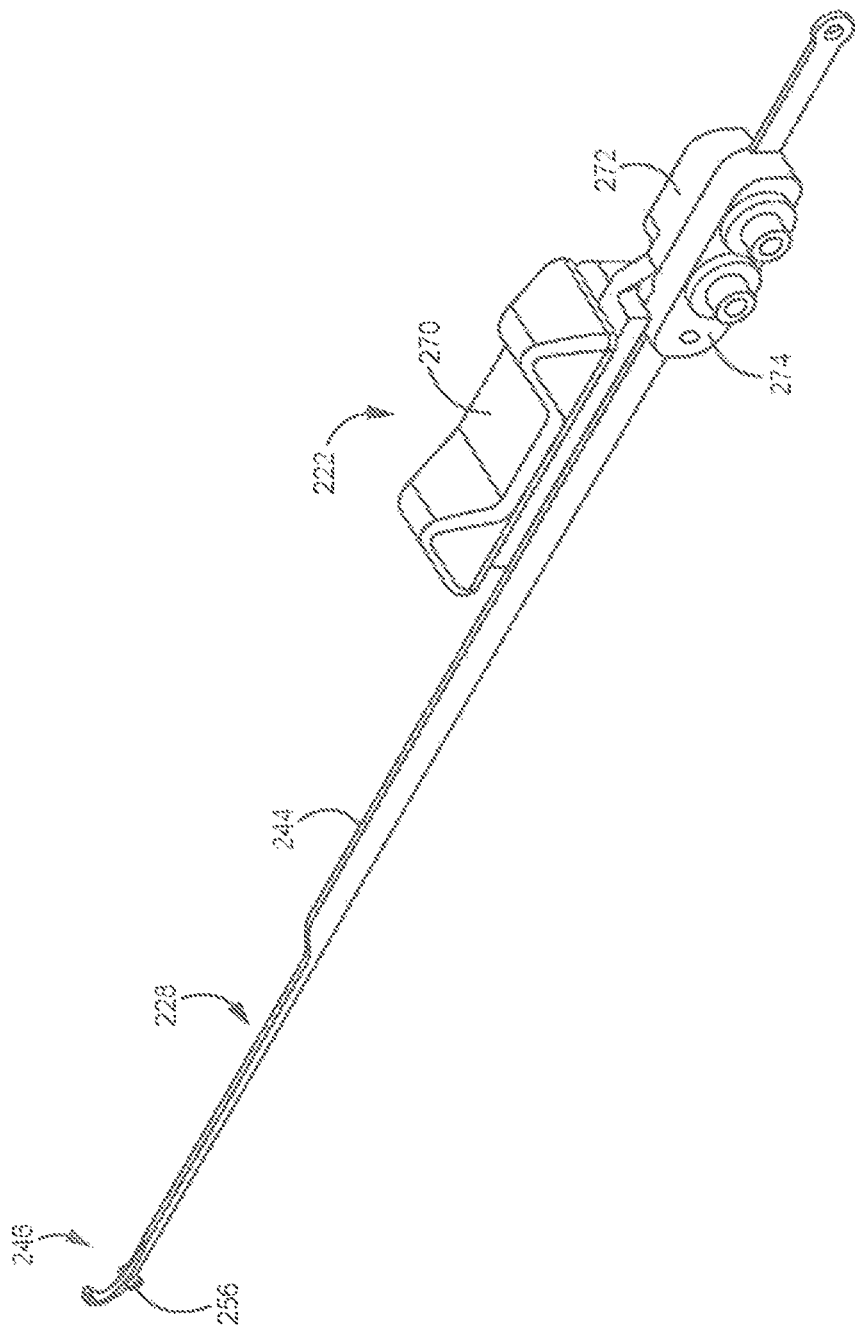
FIG. 17 illustrates a perspective view of a blade activation assembly of a soft tissue cutting device according to a third embodiment.
Figure 18:
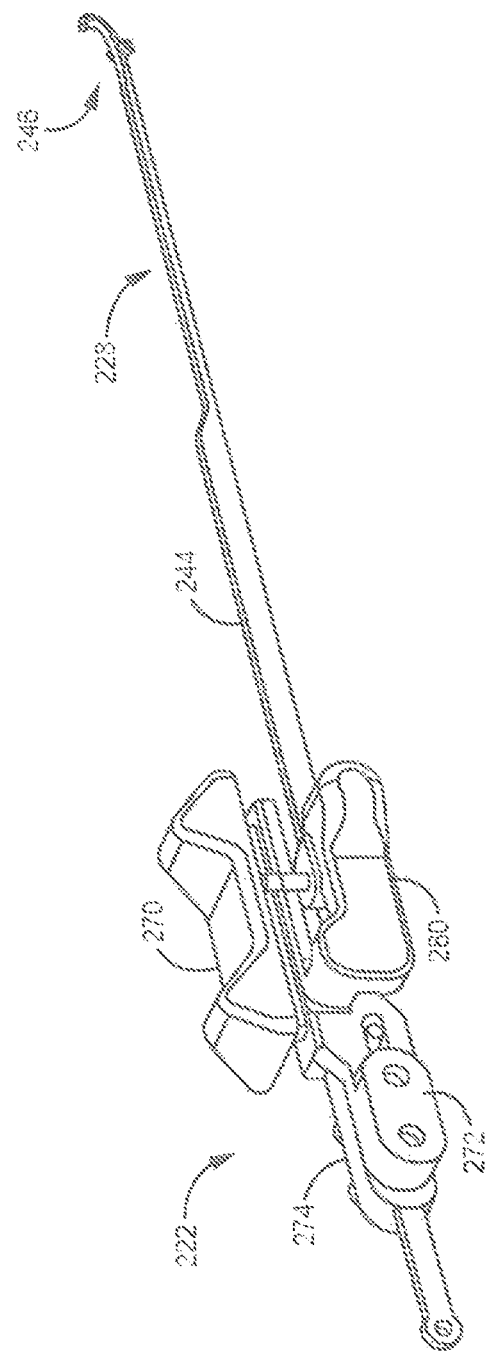
FIG. 18 illustrates another perspective view of a blade activation assembly of a soft tissue cutting device according to a third embodiment.
Figure 19:
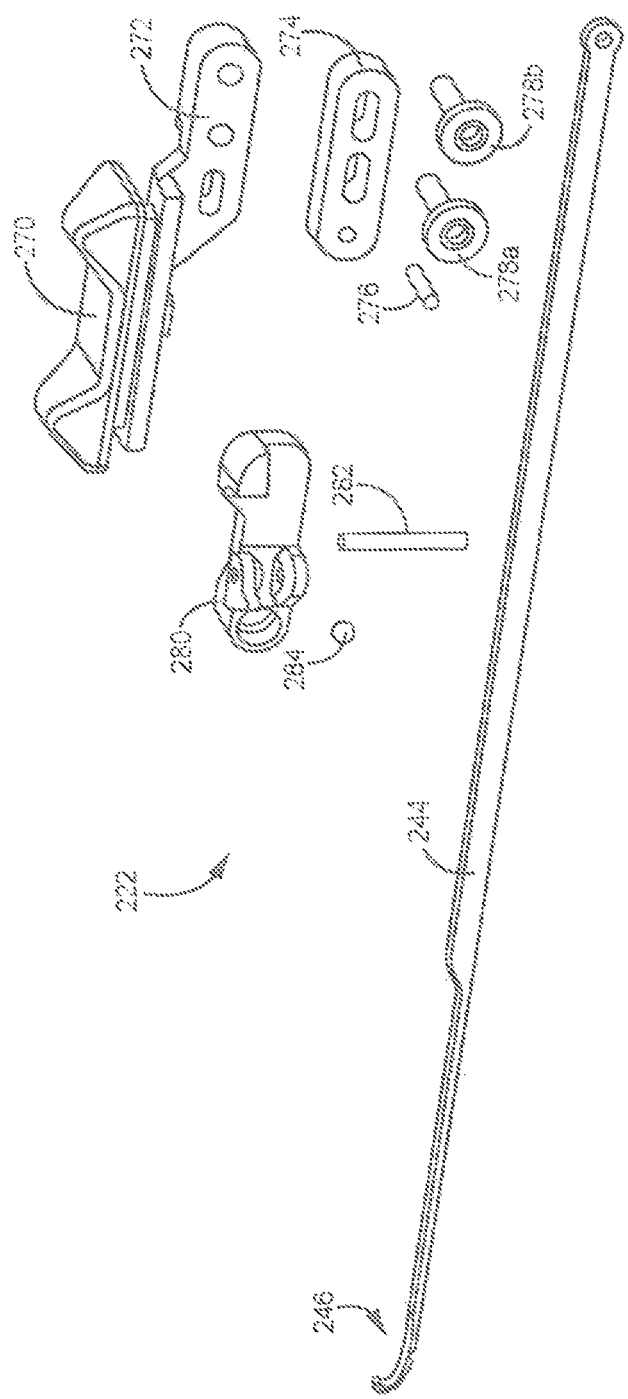
FIG. 19 illustrates an exploded view of a blade activation assembly of a soft tissue cutting device according to a third embodiment.

The shaft 220 also houses a blade 228. Referring to FIGS. 17-19, the blade 228 includes a blade shaft 244 and a blade working end 246. The blade shaft 244 engages with a blade activation assembly 222 to move the blade 228 forward and backward. The blade working end 246 is the end that is configured to cut a transverse carpal ligament.

Figure 20:
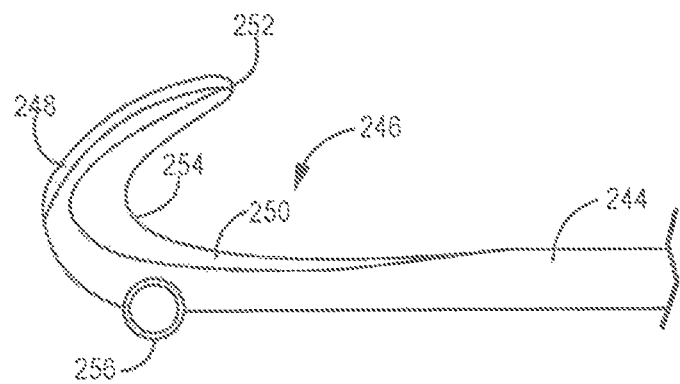
FIG. 20 illustrates a side view of a blade working end of a soft tissue cutting device according to a third embodiment.
Figure 21:
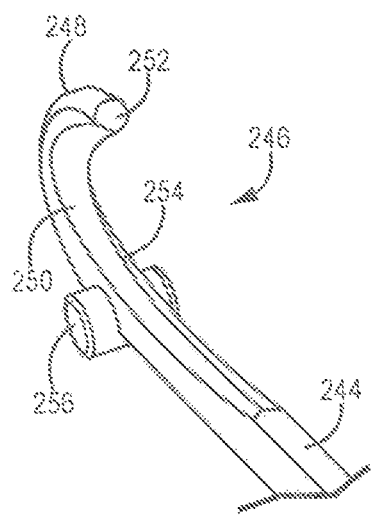
FIG. 21 illustrates a perspective view of a blade working end of a soft tissue cutting device according to a third embodiment.

FIGS. 20-21 illustrate a blade working end 246 according to an embodiment. In this embodiment, the blade working end 246 is configured as a hook. The hook includes an outer surface 248 and an inner surface 250 that come together at a point 252. The inner surface 250 includes a cutting edge 254. The cutting edge 254 thus includes a non-linear edge. Instead the cutting edge 254 includes a curved edge. In other embodiments, the blade working end is configured as an angled blade having an outer surface and an inner surface. The inner surface includes an angled cutting edge.

The outer surface 248 does not include a cutting edge. Rather, at least part of the entire outer surface 248 (or substantially the entire outer surface 248 or the entire outer surface 248) is a dull and/or blunt surface that would not cut body tissue. Likewise, the point 252 is configured as a tip that would not cut body tissue. In other words, the point 252 does not have any exposed sharp edges that would cut body tissue. In some cases, the point 252 is a blunt point and/or a dull point and/or a rounded point.

The blade working end 246 also includes a blade pin 256. The blade pin 256 is positioned on the blade working end 246 such that the pin 256 moves along a blade guideway 258 (described below). In some embodiments, the blade pin 256 is positioned along the outer surface 248. The blade pin 256 can be mechanically or weldedly attached to the blade working end 246. In other embodiments, the blade pin 256 is provided as part of or integral to the blade working end 246 and is not a separate piece.

Figure 22:
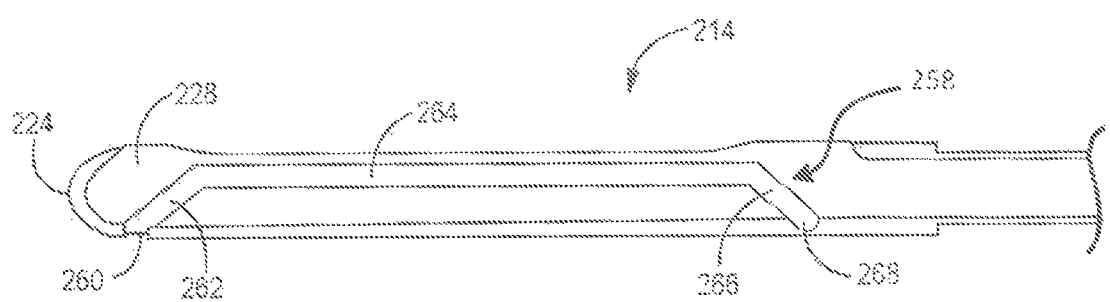
FIG. 22 illustrates a side cross-section view of a shaft of a soft tissue cutting device according to a third embodiment.

Referring to FIG. 22, the shaft 220 also includes a blade guideway 258 that guides movement of the blade 228. An operator moves the blade 228 forward and backward along the blade guideway 258. The blade guideway 258 can be any guide, groove, track or tunnel that guides the forward and rearward movement of the blade 228. The blade guideway 258 includes a distal guideway end 260, a distal incline 262, a plateau 264, a proximal incline 266 and a proximal guideway end 268. As shown, the plateau 264 is positioned between two inclines 262, 266. Also, the distal incline 262 is positioned between the distal guideway end 260 and the plateau 264. Further, the proximal incline 266 is positioned between the proximal guideway end 268 and the plateau 264. The distal incline 262 and proximal incline 266 can be configured as inclines or ramps having any desired slope. In some cases, the distal incline 262 and proximal incline 266 each have a slope angle of between 0° and 90°. In certain cases, the distal incline 262 and proximal incline 266 each have a slope angle of between 30° and 60°.

The blade 228 includes a blade pin 256 that moves within or along the blade guideway 258. FIGS. 23-26 illustrate a path of the blade pin 256 as it moves along the blade guideway 258. In FIG. 23, the blade pin 256 is positioned at the distal guideway end 260. As shown in FIG. 24, the operator moves the blade 228 backward to move the blade pin 256 up the distal incline 262. As shown in FIG. 25, the operator continues to move the blade 228 backward so that the blade pin 256 moves backward along the plateau 264. Once the blade pin 256 reaches the proximal incline 266, it moves down the proximal incline 266 until it reaches the proximal guideway end 268, as shown in FIG. 26.

When the blade pin 256 is positioned at the distal guideway end 260, as shown in FIG. 23, the cutting edge 254 of the blade 228 is housed within the shaft 220 and is not exposed through the shaft opening 226. Likewise, when the blade pin 256 is positioned at the proximal guideway end 268, as shown in FIG. 26, the cutting edge 254 is housed within the shaft 220 and is not exposed through the shaft opening 226. When the cutting edge is housed within the shaft 220, the device 200 is in an inactive or protected position.

On the other hand, when the blade pin 256 is positioned along the plateau 264, as shown in FIGS. 24-25, the cutting edge 254 of the blade 228 extends through the shaft opening 226 and is exposed. In this case, the device 200 is in an active position and is able to cut soft tissue.

Referring back to FIGS. 15-16, the shaft 220 also includes one or more balloons that expand radially outwardly from the shaft 220. The balloons can be positioned anywhere about the shaft 220 such that they expand the safe zone of the carpal tunnel region. This embodiment illustrates two lateral balloons 234a, 234b that are positioned on sides 240a, 240b of the shaft 220. The balloons 234a, 234b inflate and expand outward laterally from the shaft 220. Likewise, the balloons 234a, 234b deflate and shrink inwardly toward the shaft 220. When inflated, the balloons 234a, 234b have a spherical, oval, bilobular or other configuration. When deflated, the balloons 234a, 234b can be generally flush with the shaft 220.

The shaft 220 also optionally includes a first channel 230a and a second channel 230b. The first lateral balloon 234a can be positioned so that it lies within the first channel 230a. Likewise, the second lateral balloon 234b can be positioned so that it lies within the second channel 230b. The channels 230a, 230b can have any size and shape that accommodates the balloons 234a, 234b.

Skilled artisans will understand that any number of radially expanding balloons can be used and be placed anywhere about the shaft 220 to secure the distal end 216 in position within the carpal tunnel region and to expand the "safe zone." As the radially expanding balloons inflate, they move the flexor tendons, median nerve, and ulnar neurovascular bundle away from the device 200, effectively increasing the "safe zone." This helps to ensure that only the transverse carpal ligament is cut and that nearby at-risk structures are not cut.

The device 200 also includes a blade activation assembly 222. FIGS. 17-19 illustrate an embodiment of a blade activation assembly 222. The blade activation assembly 222 includes a slider button 270, a first plate 272, a second plate 274, a plate pin 276, a first screw 278a, a second screw 278b, a blade latch 280, a blade latch pin 282 and a ball 284. The slider button 270 is positioned on an external surface of the handle 216. An operator engages the slider button 270 with a finger (for example by engaging a thumb with the slider button 270). The operator pulls the slider button 270, which allows the guide pin 256 to slide away from the distal guideway 260 within the guideway incline 262 until reaching the end point of the proximal guideway 268. The slider button 270 can move in both forward and backward directions to move the blade 228 forward and backward.

Figure 27:
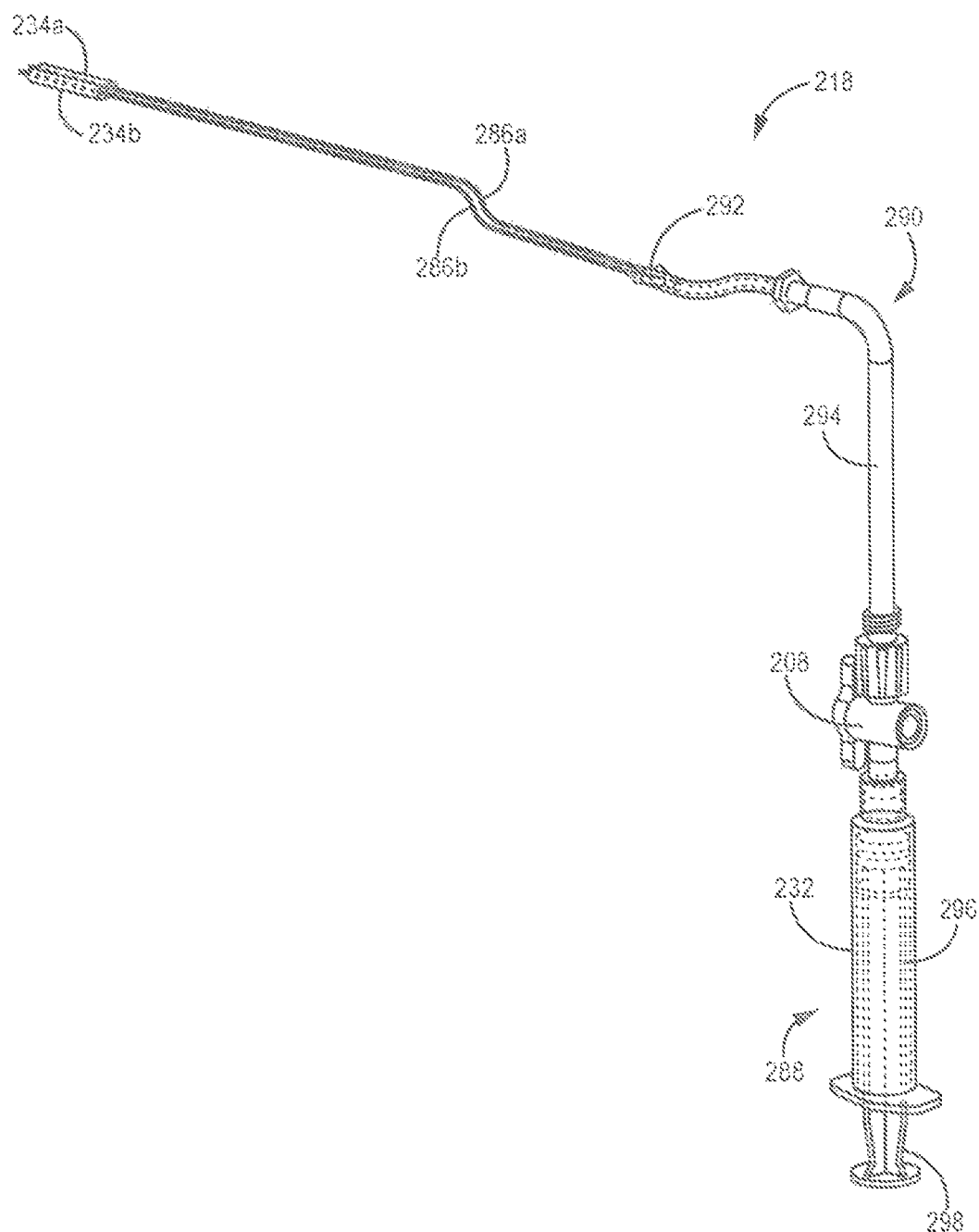
FIG. 27 illustrates a perspective view of an inflation assembly of a soft tissue cutting device according to a third embodiment.

The device 200 also includes an inflation assembly 218. The inflation assembly 218 includes the first balloon 234a, a first conduit 286a, the second balloon 234b, a second conduit 286b, and an inflation device 288. The inflation device 288 can be provided inside of the handle 216 and/or provided outside of the handle 216. FIG. 27 illustrates an embodiment of an inflation assembly 288 that is provided outside of the handle 216. Skilled artisans will also understand that the inflation assembly 218 described in this embodiment can also be included in any of the other device embodiments (e.g., device 10, 100) described herein.

The first conduit 286a connects the first balloon 234a to the inflation device 288. Likewise, the second conduit 286b connects the second balloon 236b to the inflation device 288. The inflation device 288 supplies inflation material such as gas, fluid, water or air to each the first conduit 286a and second conduit 286b, which in turn supply the inflation material to the first balloon 234a and the second balloon 234b. The inflation material causes the first balloon 234a and the second balloon 234b to inflate. The inflation device 288 also retracts inflation material from the first balloon 234a and second balloon 234b back through the first conduit 286a and second conduit 286b and back into the inflation device 288. Thus, the inflation device 288 inflates and deflates the balloons 234a, 234b.

In some embodiments, the first conduit 286a and the second conduit 286b directly connect to the inflation device 288. In other embodiments, a piping arrangement 290 is provided between the first conduit 286a, the second conduit 286b and the inflation device 288. For example, as shown in FIG. 27, each the first conduit 286a and the second conduit 286b connect to a coupling 292. In some cases, the coupling 292 is a y-shaped coupling that splits inflation material into the first conduit 286a and second conduit 286b when the material is moving towards the balloons 234a, 234b. Likewise, the coupling 292 can combine inflation material from the first conduit 286a and the second conduit 286b into a single conduit 294 when the material is moving back towards the inflation device 288. Such a piping arrangement 290 can provide increased efficiency of movement of the inflation material.

The first balloon 234a connects to the first conduit 286a and the second balloon connects 234b to the second conduit 286b. In some embodiments, the first balloon 234a directly attaches to the first conduit 286a and the second balloon 234b directly attaches to the second conduit 286b, although this is not required. In certain cases, the first conduit 286a is positioned inside of the first balloon 234a and the second conduit 286b is positioned inside of the second balloon 234b. Each conduit 286a, 286b includes a plurality of openings 202 that open into the balloons 234a, 234b.

FIG. 15 illustrates one embodiment showing a conduit positioned inside of a balloon. In FIG. 15, the second conduit 286b is shown positioned inside of the second balloon 234b. The second conduit 286b includes a plurality of openings 202 that open into the inside of the second balloon 234b. Inflation material moves in and out of these openings 202. Although not seen in FIG. 15, the first balloon 234a can connect to the first conduit 286a in a similar or identical manner.

The balloons 234a, 234b can have any desired configuration that allows them to inflate and deflate. In some embodiments, the entire balloon is expandable and thus inflates and deflates. In other embodiments, only part of the balloon is expandable. For example, the balloon can have a fixed portion and an expandable portion. FIG. 15 illustrates an embodiment wherein the balloon 234b has a fixed portion and an expandable portion 206. The fixed portion 204 can be the portion that directly attaches to conduit 286b whereas the expandable portion 206 does not directly attach to the conduit 286b and instead expands freely of the conduit 286b.

The balloons 234a, 234b also inflate to a desired size selected to accommodate the size of a patient's wrist (and thus the patient's carpal tunnel region). For example, in some cases, the balloons 234a, 234b can be provided with a specific size such that when they are fully inflated, they have a specific inflated size. In one embodiment, each of the balloons 234a, 234b inflate to a similar or same diameter (e.g., a diameter of about 1.5 mm). In patients with larger wrists, larger balloons can be used. In patients with smaller wrists, smaller balloons can be used. In another embodiment one of the balloons 234a, 234b inflates to one size and another inflates to a different size. In other cases, the balloons 234a, 234b can have a standard size but can be partially inflated or fully inflated to have a variety of different inflated sizes. In some cases, the balloon inflation can be graded to allow the operator to choose a particular balloon diameter. In certain cases, the balloon inflation can be pressure dependent, such that the balloon manually or automatically inflates until a specific pressure is exerted on the balloon surface.

The inflation device 288 can be any desired device known in the art that holds inflation material and both pushes inflation material out of the inflation device 288 and pulls inflation material back into the inflation device 288. In FIG. 27, the inflation device 288 is a syringe 232. Skilled artisans will understand that the illustrated syringe 232 is merely one embodiment of an inflation device 288 and that other devices are suitable. Also, in the illustrated embodiment, the syringe 232 is provided outside of the handle 216. However, skilled artisans will understand that the syringe 232 can instead be provided inside of the handle 216. The syringe 232 can be provided by itself or as part of a syringe control assembly (e.g., as a part of a syringe control assembly 324 described with reference to FIGS. 28-32).

The syringe 232 includes a barrel 296 and a plunger 298. The syringe 232 holds fluid inside of the barrel 296. When the operator desires to inflate the balloons 234a, 234b, he or she pushes the plunger 298 to push fluid into the piping arrangement 290 (or directly into the conduits 286a, 286b). The fluid moves into the conduits 286a, 286b and exits through the openings 202 into the balloons 234a, 234b. When the operator desires to deflate the balloons 234a, 234b, he or she pulls or retracts the plunger 298 to pull fluid back towards the inflation device 288. This causes fluid to move out of the balloons 234a, 234b through the openings 290 and back into the conduits 286a, 286b.

During use, an operator first obtains a device 200 that is in the first inactive position. In the first inactive position, the device 200 has its blade 228 positioned such that the blade pin 256 is positioned at the distal guideway end 260 of the blade guideway 258 as shown in FIG. 23. The cutting edge 254 is fully housed and protected within the shaft 220 and the device 200 can be safely inserted into a carpal tunnel region. The device 200 also has its balloons 234a, 234b in a deflated configuration. The operator inserts the distal end 214 into a carpal tunnel region such that the transverse carpal ligament is positioned adjacent the top surface 238 of the shaft 220. The operator then activates a control to cause the balloons 234a, 234b inflate and to expand the safe zone within the carpal tunnel region.

The operator next moves the slider button 270 backward to move the blade working end backward and up the distal incline 262 as shown in FIG. 24. Once the blade working end reaches the plateau as shown in FIG. 25, the cutting edge 254 is fully exposed and able to cut the transverse carpal ligament. The operator continues to move the slider button 270 backward to move the blade working end (and cutting edge) backward along the plateau 264. As the cutting edge 254 moves backward, it cuts the transverse carpal ligament.

The operator continues to move the slider button 270 backward to move the blade working end backward and down the proximal incline 266. The blade 228 stops moving backward once the blade pin 256 reaches the proximal guideway end 268 as shown in FIG. 26. Once the blade pin 256 reaches the proximal guideway end 268, the transverse carpal ligament is cut and the device 200 is in the second inactive position. The operator then activates a control to cause the balloons 234a, 234b to deflate. In this second inaction position, the device 200 has its blade 228 positioned such that the blade pin 256 is positioned at the proximal guideway end 268 of the blade guideway 258 as shown in FIG. 23. The cutting edge 254 is fully housed and protected within the shaft 220 and the device 200 can be safely removed from the body.

In certain embodiments, the handle also houses the syringe. In such cases, the syringe includes an actuator or control positioned outside of the handle that controls functions of the syringe. For example, the control can be a lever, slider button, push button and/or clamp. In some cases, the control is another slider button positioned on an external surface of the handle. The slider button can be coupled to a plunger to control movement of the plunger. In some cases, the slider button is directly connected to the plunger. In other cases, the control is a clamp. In such cases, the clamp can be coupled to a plunger to control movement of the plunger. When an operator desires to inflate the balloons, he or she slides the slider button forward (or compresses the clamp) to push the plunger and push fluid from the barrel into a piping arrangement. When the operator desires to deflate the balloons, he or she slides the slider button backward (or decompresses the clamp) to retract the plunger and retract fluid back into the barrel.

Figure 28:
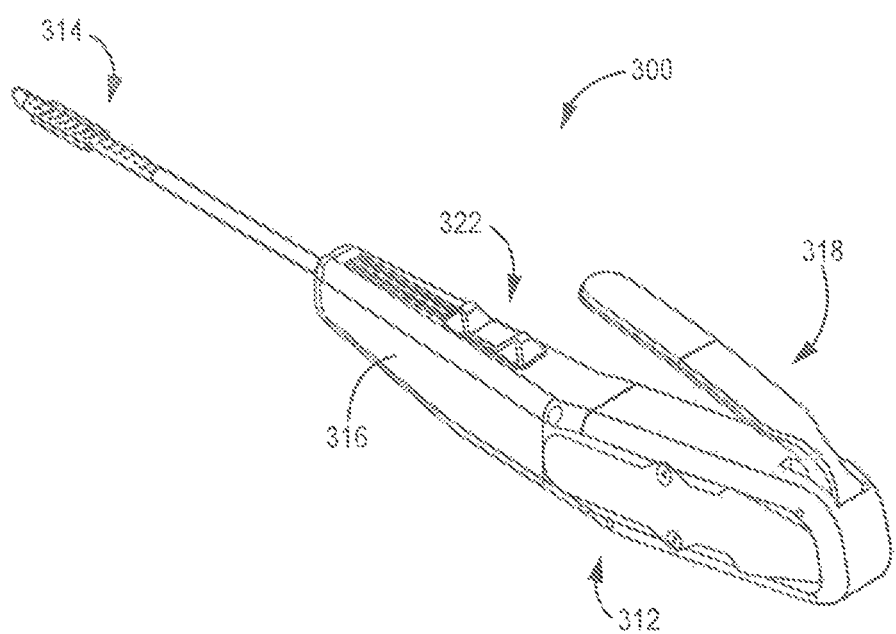
FIG. 28 illustrates a perspective view of a soft tissue cutting device according to a fourth embodiment.

FIGS. 28-32 illustrate views of a transverse carpal ligament cutting device 300 according to another embodiment. Referring to FIG. 28, the device 300 has a proximal end 312 and a distal end 314. The proximal end 312 includes a handle 316. The distal end 314 includes a shaft that inserts into the carpal tunnel region. The handle 316 includes a blade activation assembly 322. The device 300 also includes an inflation assembly 318 coupled to the handle 316. The inflation assembly 318 and blade activation assembly 322 each control various functions of the shaft at the distal end 314.

The soft tissue cutting device or transverse carpal ligament cutting device 300 includes a distal end 314 including a shaft. In some embodiments, the distal end 314 can be in accordance with the distal end 214 already described with reference to FIGS. 15-16 and 22-26. In such cases, the distal end 314 includes one or more or all of the components and functions of distal end 214.

The device 300 also includes a blade activation assembly 322. In some embodiments, the blade activation assembly 322 can be in accordance with the blade activation assembly 222 already described with reference to FIGS. 17-19. In such cases, blade activation assembly 322 includes one or more or all of the components and functions of blade activation assembly 222. Likewise, the blade activation assembly 322 can include a blade in accordance with the blade 228 already described with reference to FIGS. 17-19 and 20-21. In such cases, blade of device 300 includes one or more or all of the components and functions of blade 228.

The device 300 also includes an inflation assembly 318. The inflation assembly 318 includes one or more or all of the components and functions already described for the inflation assembly 218. For example, in FIG. 29, the inflation assembly 318 is shown as including at least the first balloon 234a, a first conduit 286a, the second balloon 234b and a second conduit 286b.

Figure 29:
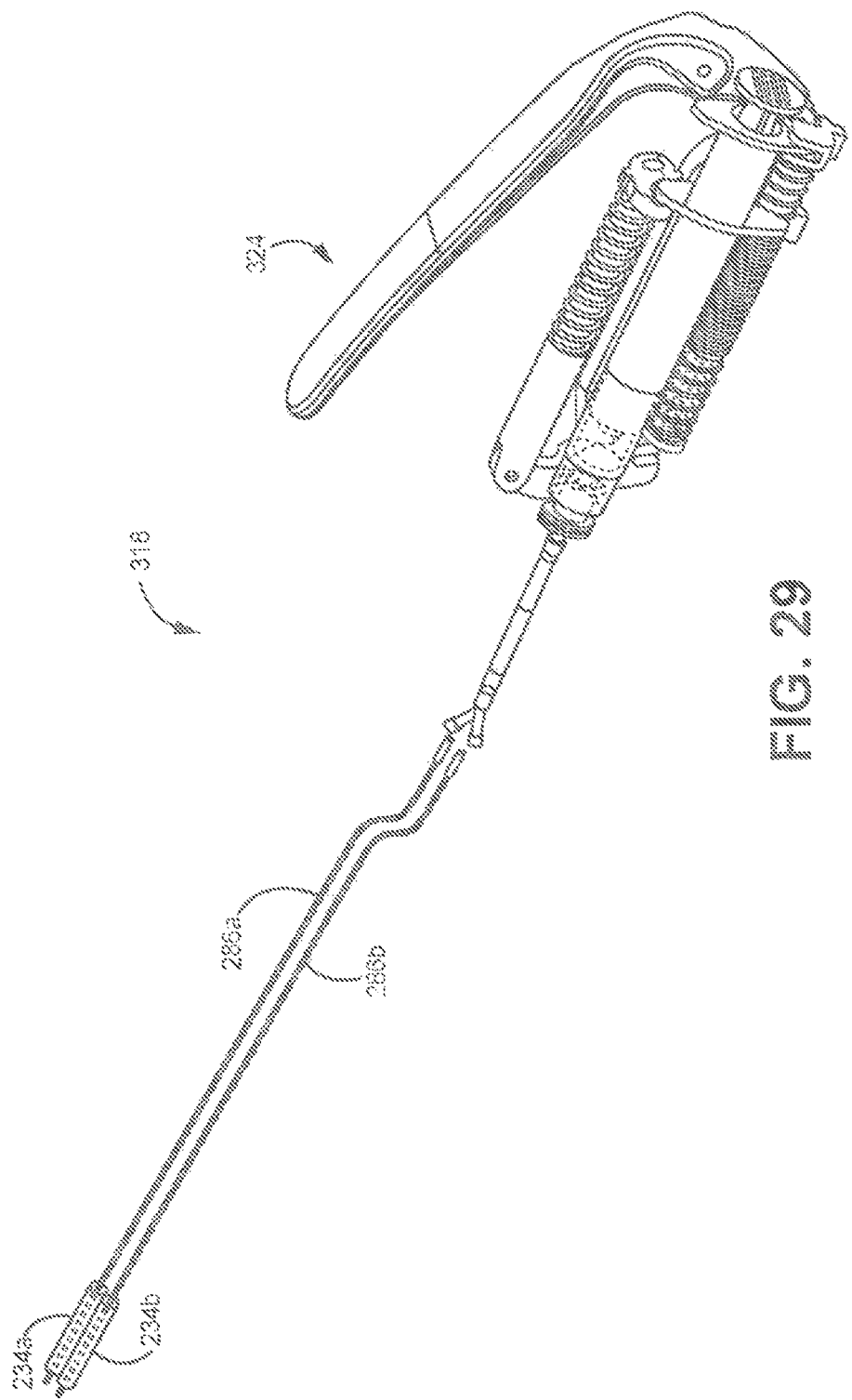
FIG. 29 illustrates a perspective view of an inflation assembly of a soft tissue cutting device according to a fourth embodiment.
Figure 30:
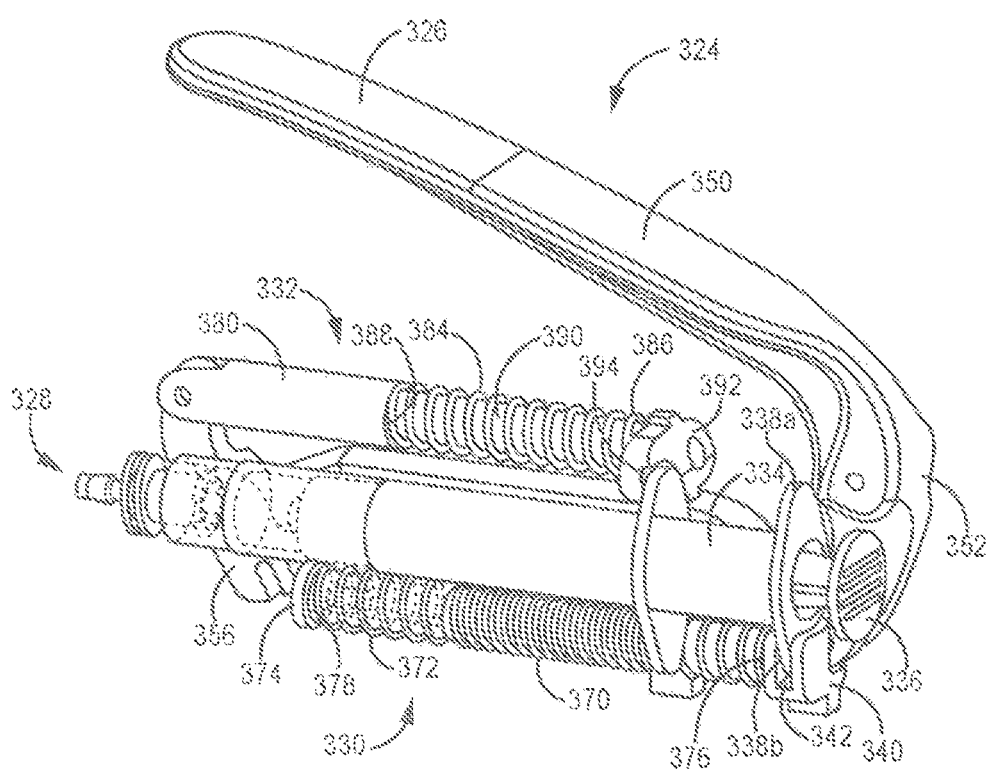
FIG. 30 illustrates a perspective view of a syringe activation assembly of a soft tissue cutting device according to a fourth embodiment.
Figure 31:
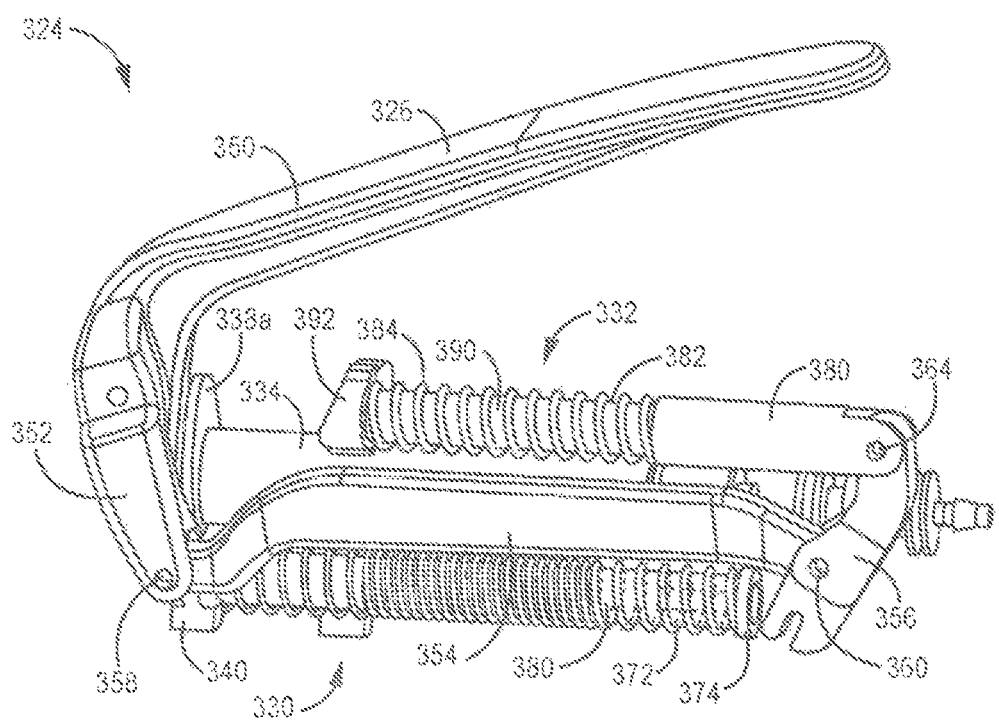
FIG. 31 illustrates another perspective view of a syringe activation assembly of a soft tissue cutting device according to a fourth embodiment.
Figure 32:
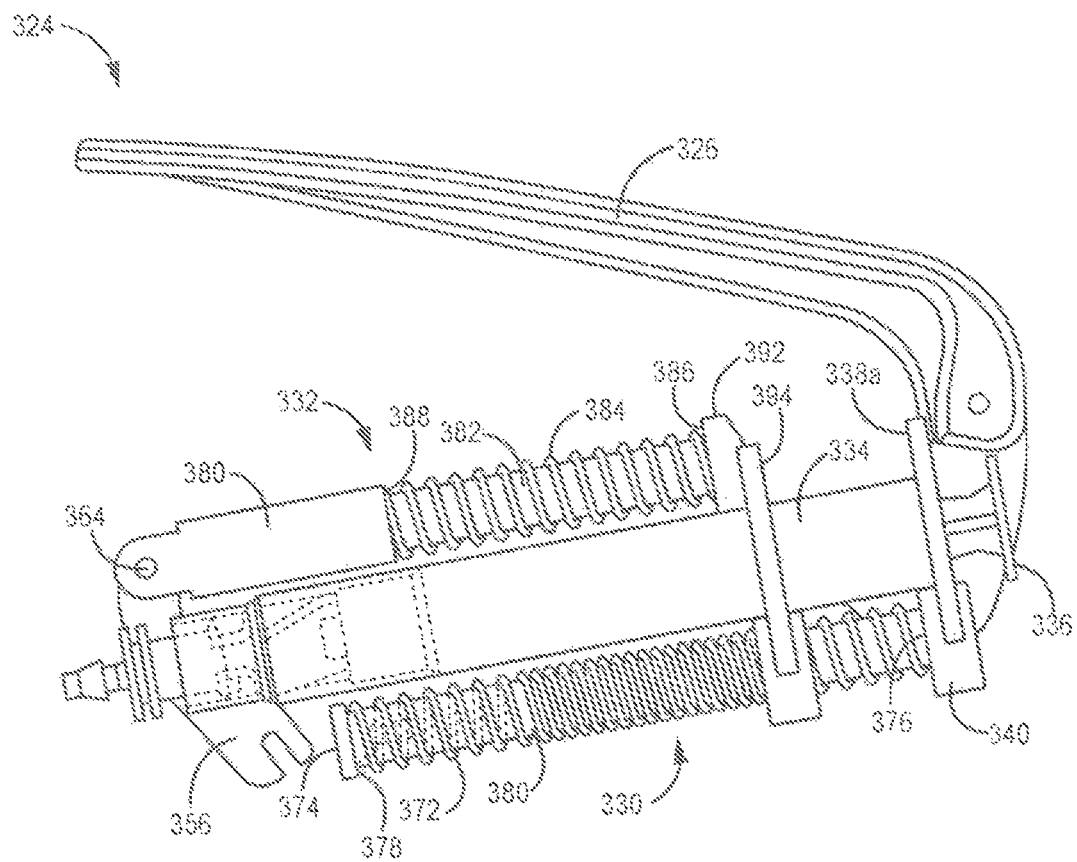
FIG. 32 illustrates a side view of a syringe activation assembly of a soft tissue cutting device according to a fourth embodiment.

The inflation assembly 318 includes an inflation device. In some cases, the inflation device includes a syringe 238 that is part of a syringe control assembly 324. FIGS. 29-31 illustrate a syringe control assembly 324 according to one embodiment. The syringe control assembly 324 includes a clamp 326, a syringe 328, a decompression mechanism 330 and a compression mechanism 332. Generally, when the operator desires to inflate the balloons 234a, 234b, he or she engages with the clamp 326 to cause the decompression mechanism 330 push fluid into the conduits 286a, 286b. When the operator desires to deflate the balloons 234a, 234b, he or she reengages with the clamp 326 to cause the compression mechanism 332 pull fluid back towards and into syringe 328. This causes fluid to move out of the balloons 234a, 234b and back into the conduits 286a, 286b.

The syringe 328 includes a barrel 334 and a plunger 336. The barrel 334 moves forward distally and backward proximally with respect to the plunger 336. In some cases, the plunger 336 is fixed in position within the handle 316 and the barrel 334 moves forward distally and backward proximally with respect to the fixed plunger 336.

In certain cases, the barrel 334 also includes a flange 338. The flange 338 at least partially expands radially outward from the barrel 330. In some cases, the flange 338 expands radially outwardly on a first side and a second side such that there is a first flange portion 338a on the first side and a second flange portion 338b on the second side.

The syringe control assembly 324 includes a decompression mechanism 330. The clamp 326 is operably coupled to the decompression mechanism 330 such that when the clamp 326 is engaged, the decompression mechanism 330 causes the barrel 334 to move backward proximally with respect to the plunger 336. This causes the plunger 336 to move deeper into the barrel 334, thus pushing fluid in the barrel 334 out of the syringe 328 and into the balloon conduits. In some cases, the decompression mechanism 330 is operably coupled to a barrel holder 340 to move the first flange portion 338a and/or the second flange portion 338b forward distally and backward proximally.

The syringe control assembly 324 also includes a compression mechanism 332. The clamp 326 is operably connected to the compression mechanism 332 such that when the clamp 326 is reengaged, the compression mechanism 332 causes the barrel to move forward distally with respect to the plunger 336. This causes the plunger 336 to move out of the barrel 334 such that it pulls fluid out of the balloon conduits and back into the barrel 334. In some cases, the compression mechanism 332 is operably coupled to a barrel plate 392 to move the first flange portion 338a and/or the second flange portion 338b forward distally and backward proximally.

In some embodiments, as best illustrated in FIG. 31, the clamp 326 includes a hand-engaging portion 350 and an arm-connecting portion 352. The arm-connecting portion 352 couples to an arm 354. The arm 354 in turn couples to a connector 356. In some cases, the arm 354 couples to the arm-connecting portion 352 via a connection 358. Likewise, the arm-connecting portion 354 couples to the connector 356 via a connection 360. Further, the connector 356 couples to the compression mechanism 332 via a connection 364. In some cases, one or more or all of the connections 358, 360, 364 are hinged connections.

The compression mechanism 332 includes a lumen 370, a spring 372 and a cap 374. The lumen 370 includes a proximal end 376 and a distal end 378. The lumen 370 also includes an outer surface 380. The spring 372 is wound about the outer surface 380 of the lumen 370. A cap 374 is positioned on the distal end 378 to secure the spring 372 in place on the outer surface 380. Also, a barrel holder 340 is positioned on the proximal end 376, also securing the spring 372 in place.

The barrel holder 340 connects to the barrel 334. The barrel holder 340 connects to the second flange portion 338b. In some cases, the barrel holder 340 includes a groove 342 that retains the second flange portion 338b. The barrel holder 340 holds and moves the second flange portion 338b forward distally and resists movement backward proximally (thus moving the barrel 334 forward distally and resisting movement of the barrel 334 backward proximally).

The compression mechanism 332 also includes a piston 380, a lumen 382 and a spring 384. The lumen 382 also includes a proximal end 386 and a distal end 388 and an outer surface 390. The spring 384 is positioned between the piston 380 and the proximal end 386 and is wound about the outer surface 390. A barrel plate 392 is also positioned at the proximal end 386 to secure the spring 384 in place.

The barrel plate 392 also connects to the barrel 334. In some cases, the barrel plate 392 connects to the first flange portion 338a. In some cases, the barrel plate 392 includes a groove 394 that receives the first flange portion 338a. The barrel plate 392 holds and moves the first flange portion 338a backward proximally (thus moving the barrel 334 backward proximally).

An operator first compresses or clamps the hand-engaging portion 350 of the clamp 326, causing the arm-connecting portion 352 to move proximally via a pivot point within the arm-connecting portion 352 (not shown), which in turn pulls the arm 354 proximally. When the arm 354 moves proximally it acts on a lower portion of the connector 356 to move the lower portion proximally via a pivot point within the connector 356 (not shown). As the lower portion moves proximally, it causes the upper portion to move distally. The distal movement of the upper portion acts on the compression mechanism 332. The flange connector 392 pushes the flange 338a proximally, thereby compressing the syringe 324. The decompression mechanism 330 is also connected to the flange 338b via the barrel holder 340. The decompression mechanism 330 resists compression of the syringe 324 via the spring 372.

During use, an operator first obtains a device 300 that is in a first inactive position. In the first inactive position, the device 300 has its blade 228 positioned such that the blade cutting edge is protected within a shaft and the device 300 can be safely inserted into a carpal tunnel region. The device 300 also has its balloons in a deflated configuration. The inactive position can be any inactive position of the devices already described herein. The operator inserts the distal end 314 into a carpal tunnel region and then engages the clamp 326, thus prompting the syringe control assembly 334 and causing the balloons inflate and to expand the safe zone within the carpal tunnel region. Once cutting is completed, the operator reengages the clamp 326, thus prompting the syringe control assembly 324 to cause the balloons to deflate.

In some cases, the soft tissue cutting device also includes a safety mechanism. Such a safety mechanism can be provided in any of the embodiments already described. The safety mechanism prevents an operator from operating the device to deflate the balloons while the blade is active. In other words, the device has a locked position and an unlocked position. In the locked position, the balloons cannot be deflated. In the unlocked position, the balloons can be inflated.

Also, in some cases, the soft tissue cutting device includes an inflation device that includes multiple inflation levels. For example, in certain cases, the syringe of any of the embodiments described is a syringe that includes multiple compression levels. For example, the multiple compression levels can include a first compression level ("x" PSI), a second compression level ("x+" PSI), a third compression level ("x++" PSI) and so on. In some cases, the multiple compression levels also include a decompression level.

Certain embodiments provide a soft tissue cutting method. The method can use any of the soft issue cutting devices described herein. In one embodiment, the method includes steps of providing a soft-tissue cutting device comprising: (a) a shaft, (b) a shaft opening in the shaft, (c) a blade that extends through and withdraws from the shaft opening, (d) one or more balloons coupled to the shaft that expand radially outward from the shaft. The method can further include steps of advancing the soft-tissue cutting device to a body region, expanding the one or more balloons radially outward and extending the blade through the shaft opening to cut the soft tissue.

Other embodiments provide a method of cutting a transverse carpal ligament. The method can use any of the transverse carpal ligament cutting devices described herein. In one embodiment, the method includes the steps of providing a cutting device having an inactive position and an active position, wherein in the inactive position the device includes an unexposed blade and one or more deflated balloons and in the active position the device includes an exposed blade and one or more inflated radially-expanding balloons, advancing the device to a carpal tunnel region while the device is in the inactive position, and cutting a transverse carpal ligament while the device is in the active position.

While different embodiments of a soft tissue cutting device are described, skill artisans will understand that any of the features of one embodiment can be incorporated into the other embodiments. Any combination of the features described in any of the embodiments can be included in the soft tissue cutting device and are within the scope of the invention.

The invention claimed is:

1. A device for cutting a transverse carpal ligament in a carpal tunnel region of a patient's hand, the device comprising:
    a handle comprising a slider button;
    a shaft extending from the handle and forming a longitudinal axis;
    a shaft opening extending longitudinally along a top surface of the shaft;
    a blade guideway in the shaft;
    a blade disposed in the shaft on the blade guideway such that the blade moves along the blade guideway and thus along the longitudinal axis of the shaft in a proximal direction toward the handle and out of the shaft opening to cut the transverse carpal ligament, the blade comprising:
        a blade shaft coupled with the slider button;
        a working end comprising a cutting edge that faces proximally toward the handle; and
        a pin extending laterally from the blade working end to engage with the blade guideway; and at least one expandable member coupled with the shaft for preventing the blade from cutting tissues other than the transverse carpal ligament, wherein the blade is configured to move along the blade guideway and the shaft from a first inactive position in which the cutting edge of the blade is housed in a distal portion of the shaft to a cutting position in which the cutting edge is exposed through the shaft opening to a second inactive position in which the cutting edge is housed within a proximal portion of the shaft.

2. The device of claim 1, wherein the at least one expandable member comprises at least one balloon.

3. The device of claim 2, wherein the at least one balloon comprises:

a first balloon on a first side of the shaft; and a second balloon on a second side of the shaft.

4. The device of claim 2, further comprising a conduit in the shaft for delivering inflation fluid to the at least one balloon, wherein the conduit is configured to couple with an inflation device that is coupled with the handle.

5. The device of claim 1, wherein the blade guideway comprises a guide rail.

6. The device of claim 1, wherein the blade shaft and the blade working end are one piece.

7. The device of claim 1, further comprising:

an inflation actuator coupled with the handle for expanding the at least one expandable member.

8. The device of claim 7, wherein the inflation actuator comprises a clamp.

9. A method for cutting a transverse carpal ligament in a carpal tunnel region of a patient's hand, the method comprising:

advancing a distal end of a soft tissue cutting device into the carpal tunnel region, below the transverse carpal ligament, with the soft tissue cutting device in a first inactive position in which a cutting edge of a blade of the soft tissue cutting device is housed in a distal portion of a shaft of the soft tissue cutting device;

activating an inflation actuator on a handle of the soft tissue device to expand at least one expandable member coupled with the distal portion of the shaft to form a safe zone, locking a safety mechanism of the soft tissue cutting device to prevent the at least one expandable member from being deflated;

moving a slider proximally along the handle to move the blade proximally along a guideway in the shaft, such that the cutting edge extends out of and travels longitudinally along a shaft opening on a top of the shaft and cuts the transverse carpal ligament;

positioning the blade in a second inactive position in which the cutting edge is housed in a proximal portion of the shaft; and removing the distal end of the soft tissue cutting device from the carpal tunnel region.

10. The method of claim 9, wherein expanding the at least one expandable member comprises inflating at least one balloon.

11. The method of claim 10, wherein inflating the at least one balloon comprises:

inflating a first balloon on a first side of the shaft; and inflating a second balloon on a second side of the shaft.

12. The method of claim 11, wherein the inflation actuator is coupled with a conduit that splits into two conduits in fluid communication with the first balloon and the second balloon.

13. The method of claim 9, wherein the blade comprises a blade shaft and a blade working end that includes the cutting edge, wherein the blade shaft and the blade working end are one piece.

14. The method of claim 9, wherein moving the blade along the guideway comprises:

moving the blade up a first incline of the guideway;

moving the blade along a plateau of the guideway; and moving the blade down a second incline of the guideway.

15. The method of claim 9, wherein activating the inflation actuator comprises squeezing a clamp.

\* \* \* \* \*